United States Patent
Nguyen et al.

(10) Patent No.: US 10,157,264 B2
(45) Date of Patent: Dec. 18, 2018

(54) AIRCRAFT MEDICAL MANAGEMENT SYSTEM

(71) Applicant: The Boeing Company, Chicago, IL (US)

(72) Inventors: Daniel Nguyen, Auburn, WA (US); Jason W. Shelton, Edgewood, WA (US); Timothy McNally Mitchell, Seattle, WA (US)

(73) Assignee: The Boeing Company, Chicago, IL (US)

( * ) Notice: Subject to any disclaimer, the term of this patent is extended or adjusted under 35 U.S.C. 154(b) by 769 days.

(21) Appl. No.: 14/663,782

(22) Filed: Mar. 20, 2015

(65) Prior Publication Data
US 2016/0275260 A1    Sep. 22, 2016

(51) Int. Cl.
*G06F 19/00*    (2018.01)

(52) U.S. Cl.
CPC .................. *G06F 19/3418* (2013.01)

(58) Field of Classification Search
CPC ........ G06Q 50/22; G06Q 50/24; G06Q 10/06; G06F 19/322; G06F 19/323–19/327; G06F 19/30; G06F 19/32; G06F 19/34; G06F 19/3418; G06F 19/3481; G08G 5/0039; G08G 5/0056; G08G 5/0017; G16H 10/00; G16H 10/60; G16H 20/00; G16H 20/10; G16H 40/00; G16H 40/40; G16H 40/60; G16H 40/67; G16H 80/00; H04B 7/185; H04B 7/18506
USPC ........................................................ 705/2, 3
See application file for complete search history.

(56) References Cited

U.S. PATENT DOCUMENTS

| | | | | |
|---|---|---|---|---|
| 5,526,265 A | * | 6/1996 | Nakhla | G08G 5/0021 244/183 |
| 6,292,687 B1 | * | 9/2001 | Lowell | A61B 5/1112 600/515 |
| 6,488,029 B1 | * | 12/2002 | Hood | A61G 1/00 128/845 |
| 7,668,736 B2 | * | 2/2010 | Jones | G06Q 10/10 705/3 |
| 8,712,793 B2 | * | 4/2014 | Jones | G06Q 50/22 705/2 |
| 9,146,969 B2 | | 9/2015 | Bahrami et al. | |

(Continued)

OTHER PUBLICATIONS

Jürgen Graf, In-Flight Medical Emergencies, Deutsches Ärzteblatt International, Dtsch Arztebl Int 2012; 109(37): 591-602.*

(Continued)

*Primary Examiner* — Jason S Tiedeman
(74) *Attorney, Agent, or Firm* — Yee & Associates, P.C.

(57) ABSTRACT

A method and system for providing medical assistance onboard an aircraft is provided. A number of secure wireless connections are established between an onboard device located on the aircraft and a remote device located remotely with respect to the aircraft, to enable communications between a device operator using the onboard device and a medical professional using the remote device. Information about a medical event that occurs onboard the aircraft is sent from the onboard device to the remote device using the number of secure wireless connections. A medical assessment of the medical event by the medical professional is received at the onboard device from the remote device over the number of secure wireless connections.

20 Claims, 10 Drawing Sheets

(56) References Cited

U.S. PATENT DOCUMENTS

| | | | |
|---|---|---|---|
| 9,257,048 B1 | 2/2016 | Offer et al. | |
| 9,310,204 B2 | 4/2016 | McGregor et al. | |
| 9,721,478 B2 | 8/2017 | Wilcox et al. | |
| 9,998,203 B2* | 6/2018 | Di Costanzo | H04L 67/12 |
| 2003/0060808 A1* | 3/2003 | Wilk | A61G 3/001 |
| | | | 606/1 |
| 2003/0064704 A1* | 4/2003 | Purpura | H04B 7/18508 |
| | | | 455/404.1 |
| 2003/0069752 A1* | 4/2003 | LeDain | G06F 19/3418 |
| | | | 705/2 |
| 2003/0144579 A1* | 7/2003 | Buss | A61B 5/0002 |
| | | | 600/300 |
| 2004/0204837 A1* | 10/2004 | Singleton | G01C 21/20 |
| | | | 701/410 |
| 2005/0240423 A1* | 10/2005 | Becker | G06Q 10/10 |
| | | | 705/2 |
| 2005/0277872 A1* | 12/2005 | Colby, Jr. | A61B 5/411 |
| | | | 604/67 |
| 2007/0055416 A1* | 3/2007 | Allen | G08G 5/0013 |
| | | | 701/3 |
| 2008/0126134 A1* | 5/2008 | Jones | G06Q 50/22 |
| | | | 705/3 |
| 2009/0076855 A1* | 3/2009 | McCord | G06F 19/3418 |
| | | | 705/3 |
| 2010/0049009 A1* | 2/2010 | Muirhead | G06F 19/3418 |
| | | | 600/301 |
| 2014/0073880 A1* | 3/2014 | Boucher | A61B 1/227 |
| | | | 600/301 |
| 2014/0343765 A1* | 11/2014 | Suiter | G08G 5/0056 |
| | | | 701/18 |

OTHER PUBLICATIONS

Hamer, Mick, Death in the skies: Airlines are failing to carry basic equipment that could save the lives of passengers who fall ill (Special Report Mid-Air Emergencies), New Scientist175.2358: 10(2), Reed Business Information Ltd. (Aug. 31, 2002).*

Sand et al., Emergency medical kits on board commercial aircraft: A comparative study, Travel Medicine and Infectious Disease (2010) 8, 388e394.*

Liao, "Handling In-Flight Medical Emergencies," Journal of Emergency Medical Services, Jun. 2010, 3 pages, accessed Mar. 19, 2015. http://www.jems.com/article/patient-care/handling-flight-medical-emerge.

Chandra et al., "In-Flight Medical Emergencies," Western Journal of Emergency Medicine, vol. XIV, No. 5, Sep. 2013, pp. 499-504.

Peterson et al., "Outcomes of Medical Emergencies on Commercial Airline Flights," The New England Journal of Medicine, Issue 368, No. 22, May 2013, pp. 2075-2083.

Taschler, "For in-flight medical emergencies, airlines follow detailed game plan," Journal Sentinel, Nov. 2013, 3 pages, accessed Mar. 19, 2015. http://www.jsonline.com/business/for-in-flight-medical-emergencies-airlines-follow-detailed-game-plan-b99138188z1-232204581.html.

Chandra et al., "Be Prepared for In-Flight Medical Emergencies," American College of Emergency Physicians, ACEP News, Aug. 2010, 3 pages, accessed Mar. 19, 2015. http://www.acep.org/Clinical—Practice-Management/Be-Prepared-for-In-Flight-Medical-Emergencies/.

* cited by examiner

AIRCRAFT MEDICAL MANAGEMENT SYSTEM

BACKGROUND INFORMATION

1. Field

The present disclosure relates generally to providing medical care and, in particular, to providing medical care to people onboard an aircraft. Still more particularly, the present disclosure relates to a method and apparatus for evaluating and managing medical events that occur onboard an aircraft during flight.

2. Background

During flight, any number of passengers, crew members, pilots, co-pilots, officers, or other persons may be onboard an aircraft. As one example, during the flight of a commercial aircraft, any number of passengers may be present onboard the aircraft, in addition to at least one pilot and at least one crew member. A possibility of a medical event occurring during the flight of an aircraft may increase with the number of people onboard the aircraft and may depend on the medical histories of these people. A medical event may include one or more people experiencing any number of symptoms.

Currently available measures for providing medical assistance to a person experiencing symptoms onboard an aircraft during flight include, for example, treating the person with a medical kit on the aircraft, turning an aircraft around and flying back to the departure point, diverting the aircraft to an alternate destination, or proceeding to the original destination depending on the distance to the original destination and the severity of the symptoms.

However, some currently available medical kits require that a trained emergency physician or other type of trained medical professional use these kits. Having a trained medical professional onboard the aircraft during flight may not always be feasible. Further, measures such as turning an aircraft around and flying back to the departure point or diverting the aircraft to an alternate destination may be expensive or problematic due to factors such as, for example, without limitation, fuel consumption. In some cases, these measures may take more time than desired to provide medical care to a person and may result in the medical condition of the person worsening.

Thus, it may be desirable to provide medical assistance onboard an aircraft, while reducing the expenses associated with managing medical emergencies onboard the aircraft. Therefore, it would be desirable to have a method and apparatus that take into account at least some of the issues related to providing flight safety and managing medical events onboard aircraft, as well as other possible issues.

SUMMARY

In one illustrative embodiment, a method for providing medical assistance onboard an aircraft is provided. A number of secure wireless connections are established between an onboard device located on the aircraft and a remote device located remotely with respect to the aircraft to enable communications between a device operator using the onboard device and a medical professional using the remote device. Information about a medical event that occurs onboard the aircraft is sent from the onboard device to the remote device using the number of secure wireless connections. A medical assessment of the medical event by the medical professional is received at the onboard device from the remote device over the number of secure wireless connections.

In another illustrative embodiment, a method for providing medical assistance onboard an aircraft during flight is provided. Physiological data is generated about a person experiencing a set of symptoms during the flight using a number of medical devices in communication with an onboard device located on the aircraft. A number of secure wireless connections are established between the onboard device and a remote device to enable communications between a device operator using the onboard device and a medical professional using the remote device during the flight. The physiological data is sent from the onboard device to the remote device during the flight. A medical assessment formulated by the medical professional using the physiological data is received at the onboard device from the remote device over the number of secure wireless connections. A number of actions are performed to medically assist the person onboard the aircraft during the flight based on the medical assessment.

In yet another illustrative embodiment, an aircraft medical management system comprises an onboard device located on an aircraft. The onboard device comprises a connection manager and an interactive interface. The connection manager establishes a number of secure wireless connections between the onboard device and a remote device to enable communications between a device operator using the onboard device and a medical professional using the remote device during flight of the aircraft. The interactive interface receives a medical assessment of a person experiencing a set of symptoms during the flight from the medical professional over the number of secure wireless connections.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to provide live medical assistance onboard an aircraft. In particular, the illustrative embodiments recognize and take into account that it may be desirable to provide live, real-time medical assistance onboard an aircraft during flight to passengers onboard the aircraft experiencing symptoms during the flight. By providing this type of medical assistance, the period of time between the time at which a passenger experiencing symptoms onboard the aircraft is observed and the time at which medical care for the passenger is initiated may be significantly reduced.

The illustrative embodiments also recognize and take into account that it may be desirable to provide the airlines with a means of remote diagnostics with the goal of accessing the risk and stability of passengers onboard an aircraft. In particular, it may be desirable to provide the airlines with the means for making an educated decision as to whether to divert an aircraft to an alternate destination, turn the aircraft back around to the departure point, or continue on the predetermined flight route for the aircraft.

Thus, the illustrative embodiments provide an aircraft medical management system that provides an additional layer of passenger safety during flight by providing a means for providing live medical assistance onboard an aircraft during the flight. In one illustrative example, a number of secure wireless connections may be established between an onboard device located on the aircraft and a remote device located remotely with respect to the aircraft to enable communications between a device operator using the onboard device and a medical professional using the remote device. Information about a medical event that occurs onboard the aircraft may be sent from the onboard device to the remote device using the number of secure wireless connections. A medical assessment of the medical event by the medical professional may be received at the onboard device from the remote device over the number of secure wireless connections. A number of actions may be performed onboard the aircraft to manage the medical event based on the medical assessment.

As used herein, a "number of" items may include one or more items. In this manner, the number of secure wireless connections established between the onboard device and the remote device may include one or more secure wireless connections. Similarly, the number of actions performed onboard the aircraft may include one or more actions.

Figure 1:
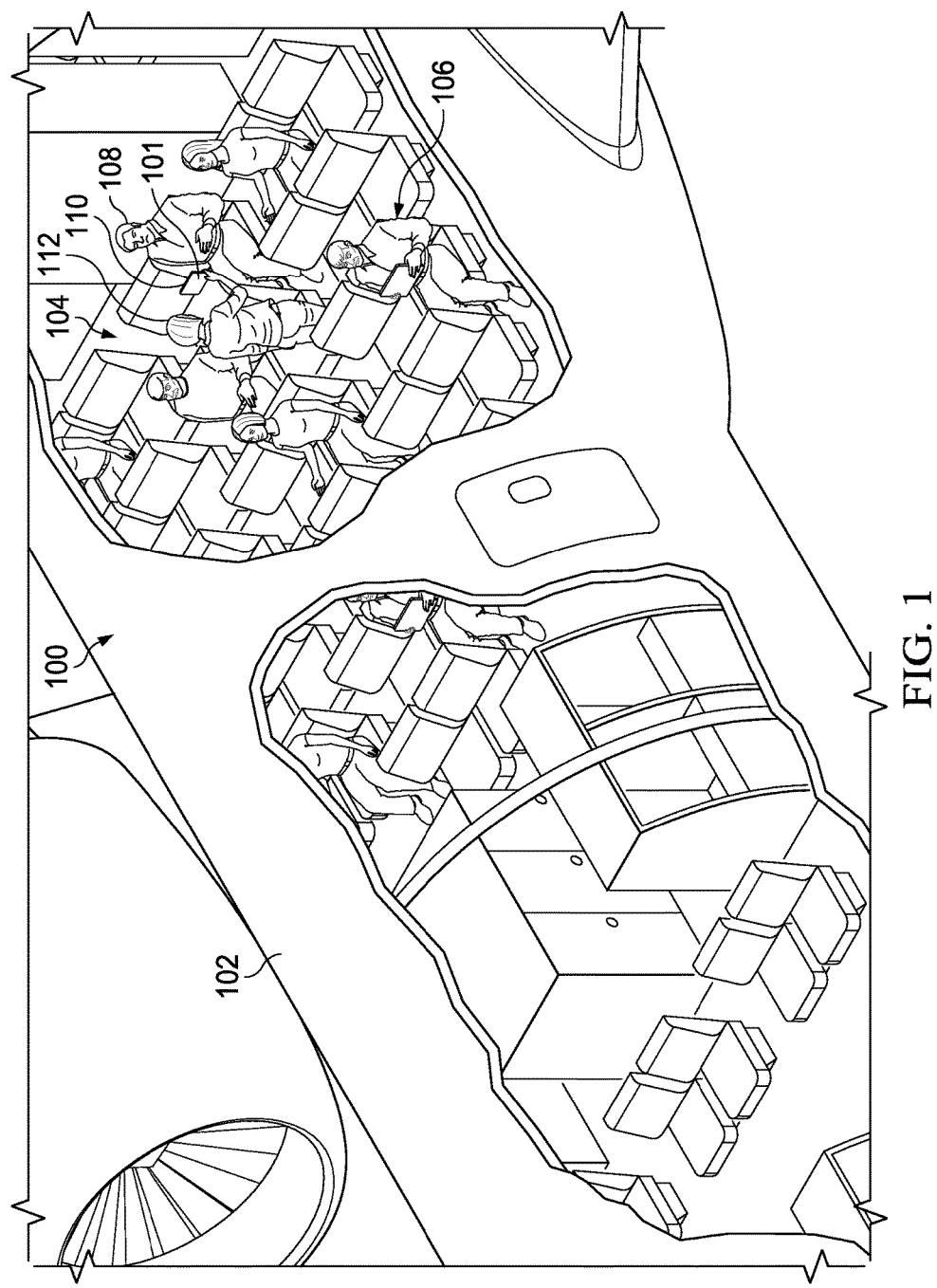
FIG. 1 is an illustration of an aircraft in accordance with an illustrative embodiment.

Referring now to the figures and, in particular, with reference to FIG. 1, an illustration of an aircraft is depicted in accordance with an illustrative embodiment. In this illustrative example, aircraft 100 may be an example of one type of aircraft with which aircraft medical management system 101 may be used. Aircraft 100 is a passenger aircraft in this illustrative example.

As depicted, aircraft 100 includes fuselage 102. Passenger cabin 104 is located within fuselage 102. Passengers 106 are present in passenger cabin 104 during flight of aircraft 100. During flight, one of passengers 106 may begin experiencing one or more symptoms.

For example, without limitation, passenger 108 may experience a fever, shortness of breath, pain, or some combination thereof. Aircraft medical management system 101 may be used to provide medical assistance to passenger 108.

As depicted, aircraft medical management system 101 includes onboard device 110. In FIG. 1, only a portion of aircraft medical management system 101 is shown. In other words, aircraft medical management system 101 may include other components in addition to onboard device 110.

Onboard device 110 takes the form of a computer tablet in this illustrative example. In other illustrative examples, onboard device 110 may take the form of a laptop, a tablet-laptop hybrid, a smartphone, a computer station onboard aircraft 100, or some other type of computing system. Onboard device 110 is used by device operator 112 to provide medical assistance to passenger 108. In this illustrative example, device operator 112 is a crew member of aircraft 102 who has a selected level of medical training and who has authorization to use onboard device 110.

However, in other illustrative examples, device operator 112 may be a medical professional, such as a physician, a nurse, a physician's assistant, or some other type of medical professional. In still other illustrative examples, device operator 112 may be any crew member with authorization to use onboard device 110, a pilot of aircraft 100, a co-pilot of aircraft 100, a passenger onboard aircraft 100, or some other person onboard aircraft 100.

Device operator 112 may use onboard device 110 to communicate with a medical professional (not shown) located on the ground. In particular, device operator 112 uses onboard device 110 to send information about passenger 108 to the physician. This information may include, for example, without limitation, personal data about passenger 108, medical history information for passenger 108, family history information for passenger 108, physiological data generated for passenger 108 using one or more medical devices onboard aircraft 100, medical permissions, medical directives, other types of information, or some combination thereof.

In some illustrative examples, device operator 112 may participate in a video conference session with the medical professional using onboard device 110. The video conference session may include audio capabilities. In some cases, this video conference session may also be used to allow the medical professional to observe passenger 108. In this manner, additional information about passenger 108 may be provided to the medical professional using onboard device 110.

The medical professional uses the information obtained about passenger 108 to provide a medical assessment of the symptoms being experienced by passenger 108. In one illustrative example, the medical professional communicates this medical assessment to device operator 112 through the video conference session. In another illustrative example, the medical professional may communicate the medical assessment to device operator 112 through an audio conference session that does not include video capabilities. In yet another illustrative example, the medical professional may communicate the medical assessment to device operator 112 by sending a report of the medical assessment to onboard device 110.

In still another illustrative example, the medical professional may communicate the medical assessment to passenger 108 directly. For example, the medical professional may verbally report the medical assessment to passenger 108 through the video conference session. In some cases, the medical professional may provide medical assistance directly to passenger 108 through the video conference session in the form of instructions.

In some illustrative examples, device operator 112 may use the medical assessment of passenger 108 by the medical professional to assist passenger 108. In particular, device operator 112 may perform one or more actions to assist passenger 108 based on the medical assessment.

Figure 2:
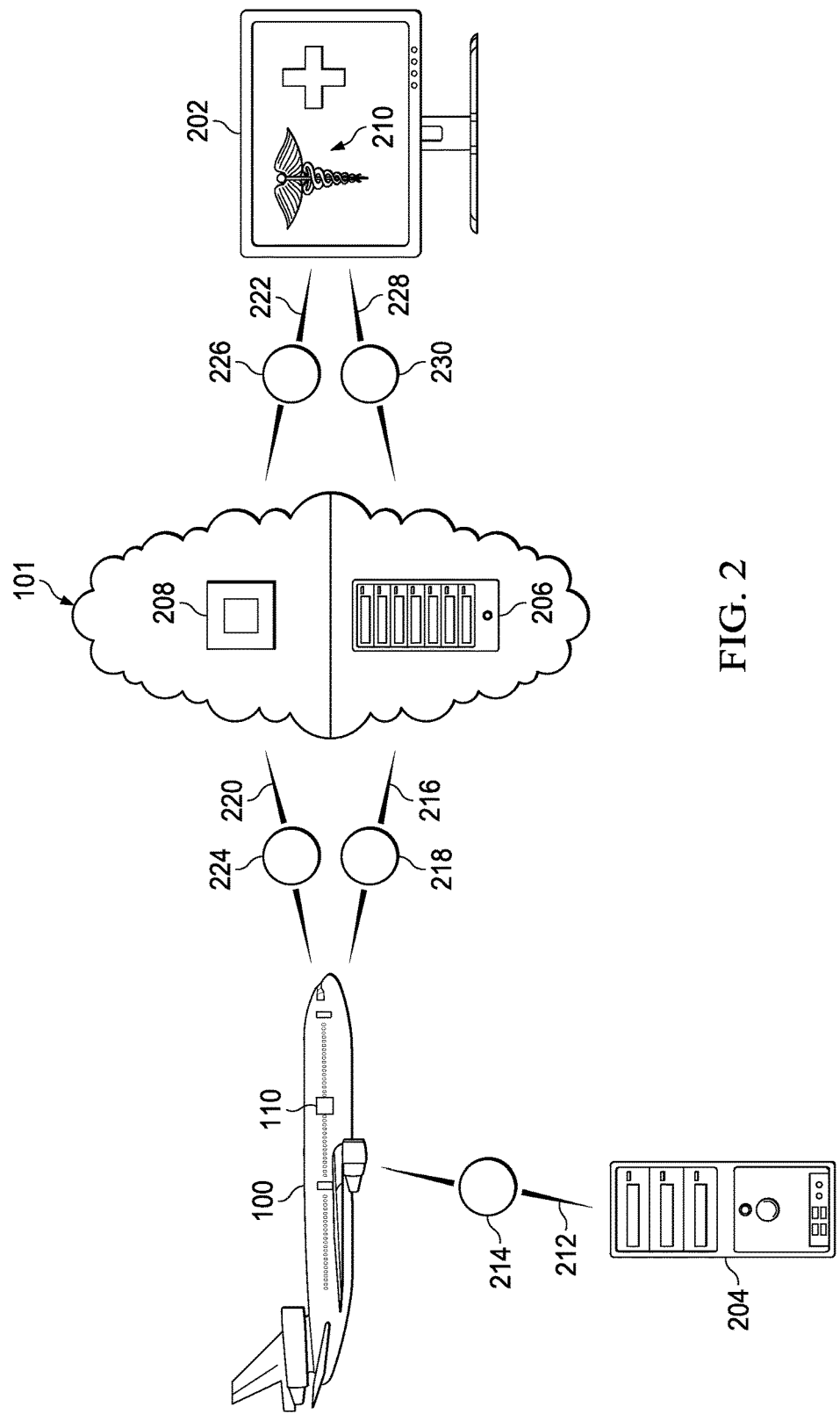
FIG. 2 is an illustration of an aircraft medical management system in accordance with an illustrative embodiment.

With reference now to FIG. 2, an illustration of aircraft medical management system 101 from FIG. 1 is depicted in accordance with an illustrative embodiment. As depicted in FIG. 2, aircraft medical management system 101 includes onboard device 110 located onboard aircraft 100. In this illustrative example, aircraft medical management system 101 also includes remote device 202, airline computer system 204, medical data storage infrastructure 206, and conference server system 208.

Remote device 202 may take a number of different forms. In one illustrative example, remote device 202 takes the form of a computer system. In other illustrative examples, remote device 202 may take the form of a laptop, a tablet, a tablet-laptop hybrid, a smartphone, an on-ground computer station, or some other type of computing system. Remote device 202 may be used by medical professional 210 as needed to provide medical assistance to one or more of passenger 106 in FIG. 1 onboard aircraft 100.

As one illustrative example, when device operator 112 in FIG. 1 becomes aware of the symptoms of passenger 108 onboard aircraft 100 in FIG. 1, device operator 112 may use onboard device 110 to communicate with medical professional 210, who may use remote device 202 to communicate with device operator 112 in FIG. 1.

In this illustrative example, device operator 112 from FIG. 1 first establishes secure wireless connection 212 between onboard device 110 and airline computer system 204. Airline computer system 204 may be comprised of one or more computers, servers, or some combination thereof.

Secure wireless connection 212 may take the form of one or more wireless communications links that allow the secure exchange of data between onboard device 110 and airline computer system 204. Airline computer system 204 may have any number of safeguards in place to ensure that any wireless connection established with airline computer system 204 is with an authorized device. For example, airline computer system 204 may have a security system that includes at least one of a firewall, an intrusion prevention system, anti-virus software, or some other type of protection for preventing unauthorized devices from wirelessly connecting to airline computer system 204. Establishing secure wireless connection 222 may include being authorized by the security system of airline computer system 204 to do so.

As used herein, the phrase "at least one of," when used with a list of items, means different combinations of one or more of the listed items may be used and only one of the items in the list may be needed. The item may be a particular object, thing, step in a process, or category. In these illustrative examples, "at least one of" means any combination of items or number of items may be used from the list, but not all of the items in the list may be required.

For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Once secure wireless connection 212 has been established, security measure 214 may need to be satisfied. Satisfying security measure 214 may include, for example, without limitation, authenticating the identify of at least one of device operator 112, onboard device 110, or aircraft 100; confirming a tail identifier for aircraft 100; authenticating aircraft 100 based on at least a portion of Out, Off, On, In (OOOI) data for aircraft 100; confirming that aircraft 100 is in-flight or in some other phase of flight; or some combination thereof.

In this illustrative example, security measure 214 is encountered and handled after secure wireless connection 212 has been established. In this manner, security measure 214 may be an additional level of security. However, in other illustrative examples, passing security measure 214 may be considered part of the process of establishing secure wireless connection 212. Thus, until security measure 214 is satisfied, onboard device 110 may be prevented from being able to access medical data storage infrastructure 206.

Medical data storage infrastructure 206 may be implemented using at least one of cloud storage, a server system comprised of one or more servers, a database, or some other type of data storage. In this illustrative example, medical data storage infrastructure 206 may only be accessible by the airline that owns and operates aircraft 100. However, in other illustrative examples, medical data storage infrastructure 206 may be accessible by a selected group of airlines.

Medical data storage infrastructure 206 stores medical data for any persons who have previously opted to have their medical data transferred to and stored in medical data storage infrastructure 206. Depending on the implementation, a person may need to opt into using medical data storage infrastructure 206 for a minimum amount of time before the scheduled departure time of the flight to allow sufficient time for the transfer of their medical data into medical data storage infrastructure 206.

As one illustrative example, the airline may request that each of passengers 106 in FIG. 1 decide whether to opt into using medical data storage infrastructure 206 at the time they book the flight. In other illustrative examples, the airline may request that each of passengers 106 decide whether to opt into using medical data storage infrastructure 206 before some selected number of days before the flight. For example, the decision may need to be made by two, three, four, ten, or some other number of days before the flight. In some cases, the decision may need to be made at least one or more weeks before the flight.

For example, passengers 106 in FIG. 1 may opt to authorize the transfer of and storage of medically relevant data in medical data storage infrastructure 206, the transfer of medical data from medical data storage infrastructure 206 to a remote device such as remote device 202, the transfer of medical data from medical data storage infrastructure 206 to an authenticated onboard device such as onboard device 210, the transfer of medical data from medical data storage infrastructure 206 to one or more on-ground medical centers, or some combination thereof. In this manner, a passenger may determine whether medical professional 210, a device operator using onboard device such as device operator 112 in FIG. 1, or both may be allowed to access the medical data of the passenger from medical data storage infrastructure 206.

The medical data stored in medical data storage infrastructure 206 may include, for example, without limitation, at least one of medical history information, medication information, previously recorded physiological data, health insurance information, family history information, mental health information, or some other type of medically relevant information. In some cases, medical data storage infrastructure 206 may include additional personal data, such as, for example, without limitation, personal contact information, emergency contact information, dietary restrictions information, dietary preference information, exercise information, other types of personal information, or some combination thereof.

In this illustrative example, once onboard device 110 establishes secure wireless connection 216 with medical data storage infrastructure 206 and security measure 218 has been satisfied, onboard device 110 may be able to access medical data storage infrastructure 206. Depending on the implementation, secure wireless connection 216 may be established and security measure 218 satisfied in a manner similar to or different from secure wireless connection 212 and security measure 214, respectively. Further, depending on the implementation, satisfying security measure 218 may be considered part of or separate from the process of establishing secure wireless connection 216.

In some illustrative examples, satisfying security measure 218 may include mutual authentication between onboard device 110 and medical data storage infrastructure 206. For example, satisfying security measure 218 may include validating a certificate for medical data storage infrastructure 206 at onboard device 110 and validating a certificate for onboard device 110 at medical data storage infrastructure 206. The request for mutual authentication may be initiated by onboard device 110 in these illustrative examples. Once security measure 218 has been satisfied, onboard device 110 may be capable of accessing medical data for passenger 108 from FIG. 1 who is experiencing symptoms.

Device operator 112 in FIG. 1 may use onboard device 110 to hold a video conference session with medical professional 210. As one illustrative example, secure wireless connection 220 is established between onboard device 110 and conference server system 208. Further, secure wireless connection 222 is established between remote device 202 and conference server system 208.

In this illustrative example, both security measure 224 and security measure 226 need to be passed in order for a video conference session to be set up through conference server system 208. Satisfying security measure 224 may include mutual authentication between conference server system 208 and onboard device 110. Satisfying security measure 226 may include mutual authentication between conference server system 208 and remote device 202.

Depending on the implementation, secure wireless connection 220 and secure wireless connection 222 may be established in a manner similar to or different from secure wireless connection 212 and secure wireless connection 216, respectively. Further, depending on the implementation, satisfying security measure 224 and security measure 226 may be considered part of or separate from the process of establishing secure wireless connection 220 and secure wireless connection 222, respectively.

Once security measure 224 and security measure 226 have been satisfied, device operator 112 in FIG. 1 may participate in a video conference session through conference server system 208 with medical professional 210 who is using remote device 202. Through the video conference session, device operator 112 in FIG. 1 can communicate with medical professional 210, explain the symptoms of passenger 108 in FIG. 1 to medical professional 210, send medical data retrieved from medical data storage infrastructure 206 for passenger 108 from onboard device 110 to remote device 202, or some combination thereof.

In some illustrative examples, medical data storage infrastructure 206 may be accessible by remote device 202. For example, without limitation, secure wireless connection 228 may be established between remote device 202 and medical data storage infrastructure 206. Once security measure 230 is satisfied, remote device 202 can access medical data storage infrastructure 206. In this manner, medical professional 210 may be able to retrieve medical data for passenger 108 directly from medical data storage infrastructure 206.

Depending on the implementation, secure wireless connection 228 may be established and security measure 230 satisfied in a manner similar to or different from secure wireless connection 216 and security measure 218, respectively. Further, depending on the implementation, satisfying security measure 230 may be considered part of or separate from the process of establishing secure wireless connection 228.

Medical professional 210 provides a medical assessment of passenger 108 through the video conference session. The medical assessment may include different types of information. For example, without limitation, the medical assessment may include at least one of a medical diagnosis for the symptoms experienced by passenger 108 in FIG. 1, instructions for isolating passenger 108 from the rest of passengers 106, instructions for treating passenger 108, instructions for communicating at least a portion of the content of the medical assessment of passenger 108 to passenger 108, an indication of the severity of the medical condition of passenger 108, an indication as to whether aircraft 100 needs to be diverted to an alternate destination, an indication of whether a medical specialist having more specialized training than the medical professional needs to be contacted, or some other type of information.

In this manner, aircraft medical management system 101 may be used to provide medical assistance to a passenger onboard aircraft 100 during any phase of flight. Aircraft medical management system 101 ensures that passengers 106 onboard aircraft 100 in FIG. 1 will have access to prompt medical assistance from a medical professional even when aircraft 100 is thousands of miles in the air.

Figure 3:
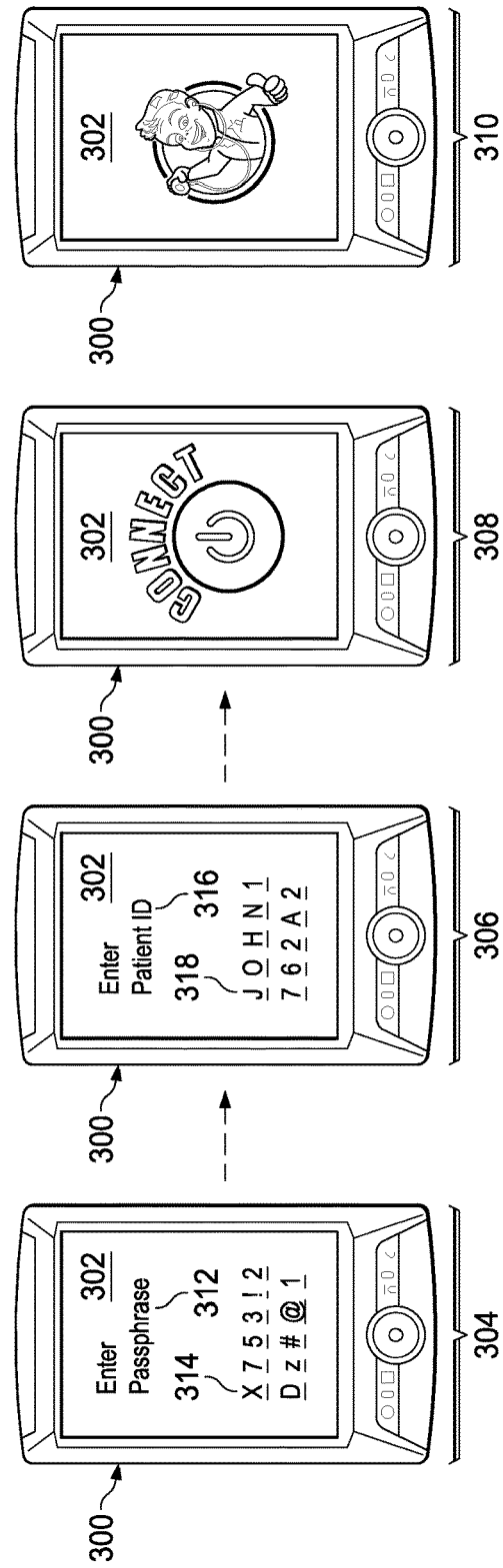
FIG. 3 is an illustration of a process for communicating with a medical professional using an onboard device in accordance with an illustrative embodiment.

With reference now to FIG. 3, an illustration of a process for communicating with a medical professional using an onboard device is depicted in accordance with an illustrative embodiment. In this illustrative example, onboard device 300 takes the form of a smartphone having display 302.

Onboard device 300 may be used onboard an aircraft, such as aircraft 100 in FIGS. 1-2, as part of an aircraft medical management system. In this illustrative example, a device operator may use onboard device 300 to communicate with a medical professional who is using a remote device on the ground. For example, device operator 112 in FIG. 1 may use onboard device 300, instead of onboard device 110 in FIGS. 1-2, to communicate with medical professional 210 in FIG. 2.

In one illustrative example, providing medical assistance to a passenger, such as passenger 108 in FIG. 1, onboard an aircraft during flight using onboard device 300 may include performing multiple steps. These steps may include, for example, but are not limited to, device authentication 304, passenger identification 306, conference session creation 308, and medical discussion 310. The results of these steps may be used to provide medical care to the passenger. For example, instructions provided by the remotely located medical professional 210 during medical discussion 310 may be used to administer treatment to or otherwise medically care for a passenger.

Device authentication 304 is performed to authenticate and validate onboard device 300 such that onboard device 300 can receive data from a medical data storage infrastructure, such as medical data storage infrastructure 206 in FIG. 2. In one illustrative example, prompt 312 is displayed on display 302 of onboard device 300. Prompt 312 is a request for a passphrase that can be used to authenticate onboard device 300. Device operator 112 enters passphrase 314 such that onboard device 300 can be authenticated. Once onboard device 300 is authenticated, onboard device 300 may be able to access medical data storage infrastructure 206.

Next, passenger identification 306 is performed. In one illustrative example, prompt 316 is displayed in display 302 of onboard device 300. Prompt 316 is a request for a passenger identifier that can be used to access the medical data specific to passenger 108. The device operator enters passenger identifier 318. Passenger identifier 318 is used to retrieve the medical data stored in medical data storage infrastructure 206 for the corresponding passenger 108.

Thereafter, conference session creation 308 is performed. This step may be performed in any number of ways. Performing conference session creation 308 may require, for example, without limitation, that a conference server system, such as conference server system 208 in FIG. 2, authenticate both onboard device 300 and remote device 202 being used by medical professional 210. The conference session may include audio, video, or both, depending on the implementation.

Once a conference session has been created such that device operator 112 from FIG. 1 using onboard device 300 can communicate with medical professional 210 using remote device 202, medical discussion 310 may ensue. Further, during the conference session, some portion of the medical data for passenger 108 retrieved from medical data storage infrastructure 206 may be sent from onboard device 300 to remote device 202 being used by medical professional 210. Medical professional 210 and device operator 112 using onboard device 300 may discuss the symptoms being experienced by passenger 108, the medical data about passenger 108, and other relevant information regarding passenger 108. In this manner, medical professional 210 may provide a medical assessment of passenger 108.

Figure 4:
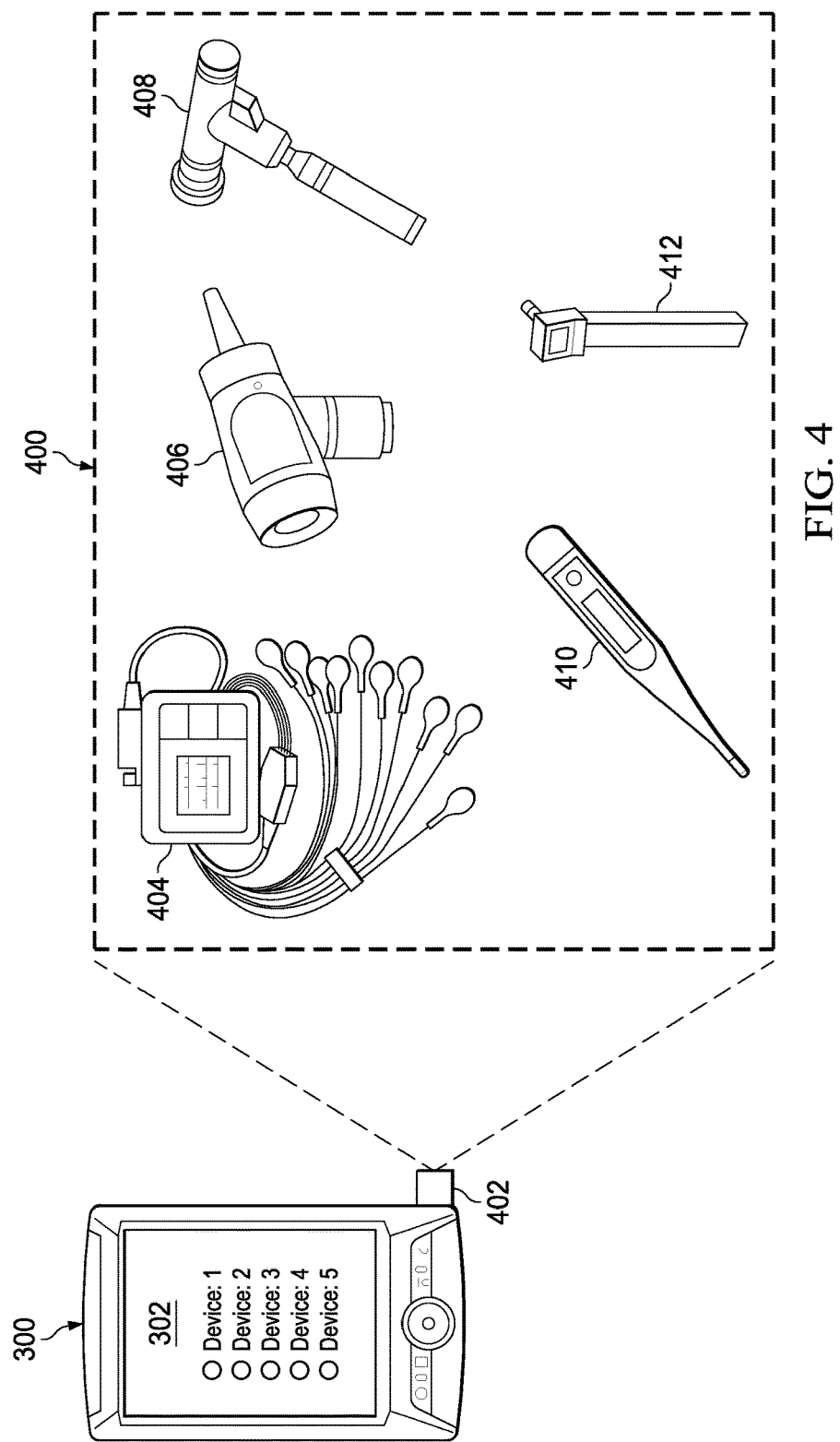
FIG. 4 is an illustration of medical devices for use with an onboard device in accordance with an illustrative embodiment.

With reference now to FIG. 4, an illustration of medical devices for use with onboard device 300 from FIG. 3 is depicted in accordance with an illustrative embodiment. In this illustrative example, each of medical devices 400 may be connected to onboard device 300 and used to generate physiological data for a person.

In this illustrative example, attachment element 402 is shown connected to onboard device 300. Each of medical devices 400 may be capable of being connected to onboard device 300 through attachment element 402. As depicted, medical devices 400 may include, but are not limited to, electrocardiogram (EKG) machine 404, otoscope 406, ophthalmoscope 408, digital thermometer 410, and tympanometric instrument 412.

The illustration of aircraft 100 in FIG. 1, aircraft medical management system 101 in FIGS. 1-2, onboard device 300 in FIGS. 3-4, and medical devices 400 in FIG. 4 is not meant to imply physical, functional, logical, or architectural limitations to the manner in which an illustrative embodiment may be implemented. Other components in addition to or in place of the ones illustrated may be used. Some components may be optional.

Figure 5:
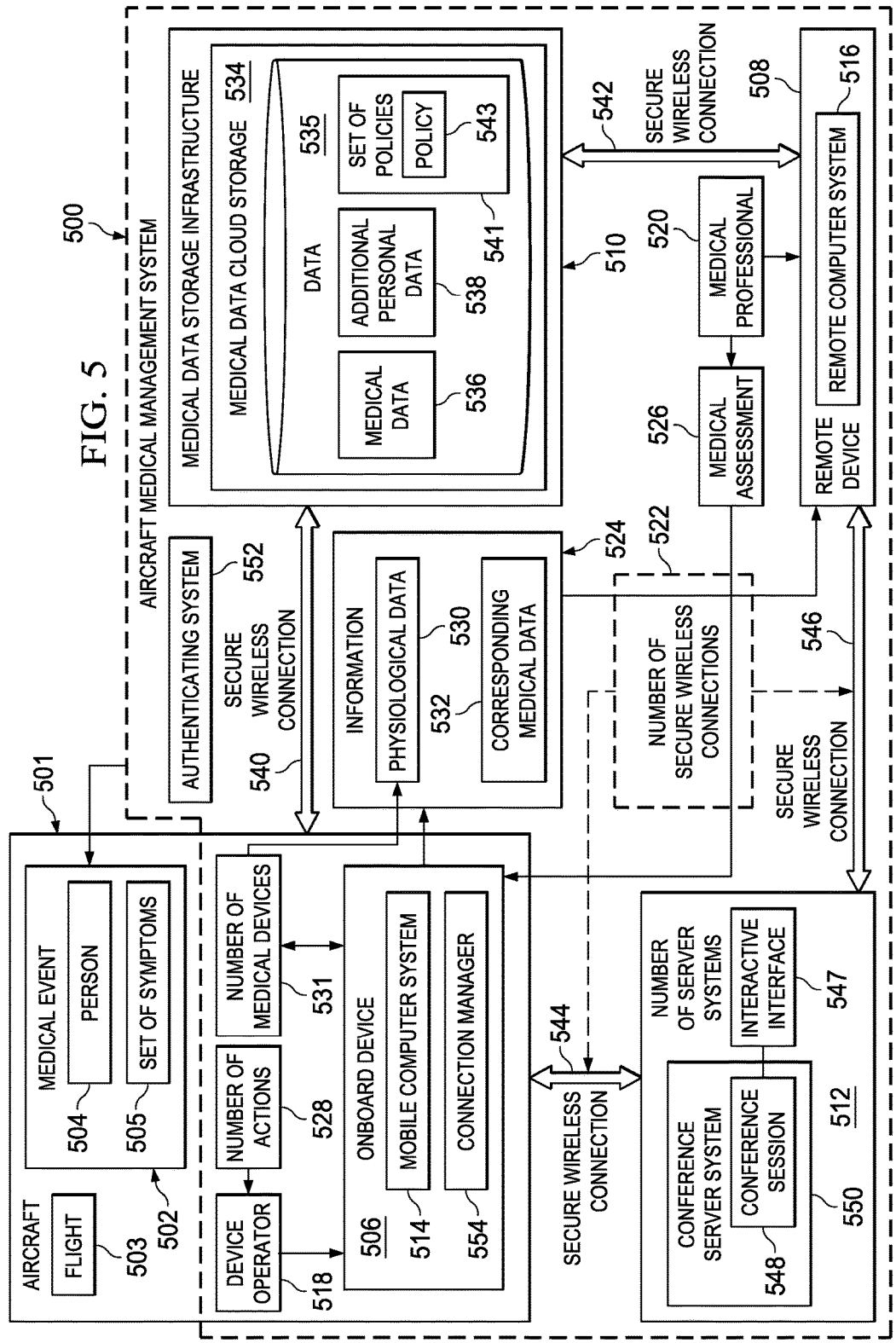
FIG. 5 is an illustration an aircraft medical management system in the form of a block diagram in accordance with an illustrative embodiment.

With reference now to FIG. 5, an illustration of an aircraft medical management system is depicted in the form of a block diagram in accordance with an illustrative embodiment. In this illustrative example, aircraft medical management system 500 is an example of a system that may be used to provide medical assistance onboard aircraft 501. Aircraft 501 may take the form of a passenger aircraft, a transportation aircraft, a medical evacuation aircraft, or some other type of aircraft.

Aircraft medical management system 101 described in FIGS. 1-2 is an example of one implementation for aircraft medical management system 500 in FIG. 5. Aircraft 100 in FIGS. 1-2 is an example of one implementation for aircraft 501 in FIG. 5.

In this illustrative example, aircraft medical management system 500 may be used to provide medical assistance to any number of people onboard aircraft 501 in response to medical event 502. Medical event 502 may occur during any one of the phases of flight 503 of aircraft 501. Aircraft medical management system 500 enables medical assistance to be provided in response to medical event 504 during taxiing, take-off, ascent, cruise, descent, landing, final approach, or some other phase of flight 503.

In one illustrative example, medical event 502 is person 504 experiencing set of symptoms 505 while person 504 is onboard aircraft 501. Person 504 may take the form of a passenger, a crew member, a pilot, a co-pilot, or some other person onboard aircraft 501. Set of symptoms 505 may include, for example, without limitation, fever, shortness of breath, pain, a headache, nausea, vomiting, skin discoloration, hearing impairment, vision impairment, tachycardia, an arrhythmia, a weakened pulse, one or more other types of symptoms, or some combination thereof. In some illustrative examples, medical event 502 may be more than one person experiencing one or more same or different symptoms.

As depicted, aircraft medical management system 500 includes onboard device 506, remote device 508, medical data storage infrastructure 510, and number of server systems 512. Onboard device 506 is located on aircraft 501, while remote device 508 is located off-board. For example, remote device 508 may be located on the ground. Depending on the implementation, medical data storage infrastructure 510 may be located onboard, off-board, or both.

Onboard device 506 may take a number of different forms. In one illustrative example, onboard device 506 takes the form of mobile computer system 514. Mobile computer system 514 may take the form of a tablet, a laptop, a tablet-laptop hybrid, a smartphone, or some other type of mobile computer system 514. In other illustrative examples, onboard device 506 may take the form of a computer system that is located in a fixed location onboard aircraft 501. For example, without limitation, onboard device 506 may be a computer system that is in a fixed location onboard aircraft 501 in an area designated for medically attending to persons onboard aircraft 501.

Similarly, remote device 508 may take a number of different forms. In one illustrative example, remote device 508 takes the form of remote computer system 516. Remote computer system 516 may take the form of a tablet, a laptop, a tablet-laptop hybrid, a smartphone, a desktop computer system, or some other type of computer system located remotely.

Device operator 518 may use onboard device 506 to communicate with medical professional 520 who uses remote device 508. Device operator 518 may be, for example, without limitation, a crew member onboard aircraft 501 who has a selected level of medical training and who has authorization to use onboard device 506. However, in other illustrative examples, device operator 518 may be a medical professional, such as a physician, a nurse, a physician's assistant, or some other type of medical professional.

In still other illustrative examples, device operator 518 may be any crew member with authorization to use onboard device 506, a pilot of aircraft 501, a co-pilot of aircraft 501, a passenger onboard aircraft 501, or some other person onboard aircraft 501. For example, when medical event 502 is an emergency medical event, a passenger may use onboard device 506 to communicate with medical professional 520 when crew member availability is limited and time is of the essence.

Device operator 518 and medical professional 520 communicate with each other through onboard device 506 and remote device 508, respectively, using one or more number of communications links. For example, number of secure wireless connections 522 may be established between onboard device 506 and remote device 508. Each secure wireless connection in number of secure wireless connections 522 may include one or more wireless communications links that allow the secure exchange of data.

In one illustrative example, number of secure wireless connections 522 may be established between onboard device 506 located onboard aircraft 501 and remote device 508 located remotely with respect to aircraft 501 to enable communications between device operator 518 using onboard device 506 and medical professional 520 using remote device 508. Information 524 related to medical event 502 is sent from onboard device 506 to remote device 508 using number of secure wireless connections 522. Medical professional 520 uses information 524 received at remote device 508 to formulate medical assessment 526 of medical event 504. Medical assessment 526 of medical event 502 by medical professional 520 is received at onboard device 506 over number of secure wireless connections 522 from remote device 508.

Medical assessment 526 may include different types of information. For example, without limitation, medical assessment 526 may include at least one of an overall medical evaluation of medical event 502, a medical diagnosis for set of symptoms 505 experienced by person 504, a number of isolation instructions for isolating person 504 from other persons onboard aircraft 501, a number of treatment instructions for treating person 504, a number of advising instructions for communicating at least a portion of the content of medical assessment 526 to person 504, an indication of the severity of the medical condition of person 504, an indication as to whether aircraft 501 needs to be diverted to an alternate destination, an indication of whether a specialist having more specialized training and expertise than medical professional 520 needs to be contacted, or some other type of information.

In response to receiving medical assessment 526, number of actions 528 may be performed based on medical assessment 526 to manage medical event 502 onboard aircraft 501. Number of actions 528 may be performed by at least one of device operator 518 or some other person onboard aircraft 501.

For example, without limitation, device operator 518 may perform number of actions 528 to assist person 504 onboard aircraft 501 experiencing set of symptoms 505. Number of actions 528 may be performed to at least one of isolate, treat, or advise person 504. Advising person 504 may include, for example, without limitation, communicating at least a portion of the content of medical assessment 526 to person 504, explaining other actions being performed by device operator 518 to assist person 504, providing other information to person 504 based on medical assessment 526, or some combination thereof.

In some illustrative examples, number of actions 528 may include changing a flight route of aircraft 501. For example, flight 503 of aircraft 501 may be diverted from a current destination of flight 505 to an alternate destination. In one illustrative example, the alternative destination is selected based on proximity to an on-ground medical center that has been selected for person 504. The alternate destination may be an airport near the on-ground medical center, an airfield or other suitable landing area near the on-ground medical center, the on-ground medical center itself, or some other type of destination. The on-ground medical center may be a hospital, a clinic, a medical facility located at an airport, or some other type of medical center.

Communications between device operator 518 using onboard device 506 and medical professional 520 using remote device 508 may be implemented in a number of different ways. In one illustrative example, information 524 related to medical event 502 may be sent directly from onboard device 506 to remote device 508 over number of secure wireless connections 522.

Information 524 may include different types of information. In some illustrative examples, information 524 may include information about aircraft 501, flight 505, onboard device 506, device operator 518, or a combination thereof. In other illustrative examples, information 524 may include physiological data 530 generated for person 504.

Physiological data 530 may be generated onboard aircraft 501 using number of medical devices 531 in communication with onboard device 506. In one illustrative example, a medical device in number of medical devices 531 may be capable of being directly connected to onboard device 506 such that data generated by the medical device is sent to onboard device 506. In other illustrative examples, a medical device in number of medical devices 531 may be used to generate data and may then wirelessly send this data to onboard device 506. In some illustrative examples, a medical device in number of medical devices 531 is used to collect physiological information about person 504. This physiological information is then manually input by device operator 518 into onboard device 506.

In these illustrative examples, number of medical devices 531 may be considered part of aircraft medical management system 500. Number of medical devices 531 may include at least one of, for example, without limitation, a digital thermometer, an electronic stethoscope, an electrocardiogram machine, a tympanometric instrument, a sphygmomanometer, an otoscope, an ophthalmoscope, a pulse oximeter, a vital signs monitor, a laryngoscope, a penlight, a diagnostic station, an x-ray machine, an ultrasound device, or some other type of medical device or instrument.

In some cases, information 524 may include corresponding medical data 532 for person 504 retrieved from medical data storage infrastructure 510. Medical data storage infrastructure 510 may be implemented using any number of different types of data storage infrastructures. In one illustrative example, medical data storage infrastructure 510 takes the form of medical data cloud storage 534. In other illustrative examples, medical data storage infrastructure 510 may be comprised of at least one of cloud storage, a database, a server system that includes one or more servers, or some other type of data storage.

As depicted, data 535 is stored in medical data storage infrastructure 510. Data 535 may include medical data 536 for one or more persons who opt to authorize the storage of medically relevant data in medical data storage infrastructure 510.

As one illustrative example, when booking a flight, registering with an airline, or registering with a medical service associated with an airline, the customers of the airline may be given the option to authorize the transfer of their medical data to medical data storage infrastructure 510, the transfer of this medical data from medical data storage infrastructure 510 to an authenticated onboard device such as onboard device 506, the transfer of this medical data from medical data storage infrastructure 510 to an authenticated remote device such as remote device 508, or some combination thereof. In this manner, a customer may determine whether medical professional 520, device operator 518, or both may be allowed to access the medical data of the customer from medical data storage infrastructure 510. Any transfer of medical data between devices and storage infrastructures is performed in accordance with federal regulations and guidelines, including, but not limited to the Health Insurance Portability and Accountability Act (HIPAA).

In this illustrative example, medical data 536 may include, but is not limited to, at least one of medical history information, medication information, previously recorded physiological data, health insurance information, family history information, or some other type of medically relevant information. In some cases, medical data storage infrastructure 510 may store additional personal data 538. Additional personal data 538 may include, for example, without limitation, at least one of personal contact information, emergency contact information, dietary restrictions information, dietary preference information, exercise information, or some other type of additional information.

In response to person 504 experiencing set of symptoms 505 onboard aircraft 501, device operator 518 may establish secure wireless connection 540 between onboard device 506 and medical data storage infrastructure 510. Secure wireless connection 540 may include one or more wireless communications links. In one illustrative example, device operator 518 uses onboard device 506 to retrieve corresponding medical data 532 from medical data storage infrastructure 510 over secure wireless connection 540. Corresponding medical data 532 may include at least a portion of medical data 536 stored in medical data storage infrastructure 510 for person 504.

In some illustrative examples, remote device 508 may have the capability of accessing medical data storage infrastructure 510 directly. For example, medical professional 520 may establish secure wireless connection 542 between remote device 508 and medical data storage infrastructure 510. Secure wireless connection 542 may include one or more wireless communications links. Medical professional 520 may access corresponding medical data 532 for person 504 directly from medical data storage infrastructure 510 in this illustrative example.

In some cases, set of policies 541 may be stored in medical data storage infrastructure 510. Each of set of policies 541 may be for a person who has opted for storing their medical data in medical data storage infrastructure 510.

For example, policy 543 in set of policies 541 may be associated with person 504. Policy 543 may include at least one of a set of rules, a set of guidelines, a set of restrictions, a set of authorizations, a set of criteria, or other information.

Policy 543 may take the form of at least one of a report, a spreadsheet, a database, a document, some other type of file, or some other type of computer resource. Policy 543 may determine which data stored in medical data storage infrastructure 510 may be accessible by an onboard device, such as onboard device 506, and which data stored in medical data storage infrastructure 510 may be accessible by a remote device, such as remote device 508.

In some illustrative example, policy 543 may determine whether any of information 524 about person 504 can be forwarded from onboard device 506 or medical data storage infrastructure 510 to an on-ground medical center selected for person 504. For example, when flight 503 has been diverted such that person 504 may be taken to a selected on-ground medical center, policy 543 may determine whether any of information 524 about person 504 may be forwarded to the selected on-ground medical center.

Person 504 may choose to provide a general authorization that allows all physiological data 530 and corresponding medical data 532 for person 504 to be forwarded to any on-ground medical center. In another example, person 504 may provide a specific authorization for which on-ground medical centers may receive this data.

In this manner, policy 543 may determine which data stored in medical data storage infrastructure 510 may be viewed by a device operator, such as device operator 518, and which data stored in medical data storage infrastructure 510 may be viewed by a medical professional, such as medical professional 520. Further, policy 543 may determine what types of information 524 about person 504 may be forwarded to on-ground medical centers.

In some illustrative examples, at least a portion of information 524 may be sent from onboard device 506 to remote device 508 through a conference session. For example, number of server systems 512 may be used to establish interactive interface 547 between onboard device 506 and remote device 508. In particular, secure wireless connection 544 may be established between onboard device 506 and number of server systems 512. Secure wireless connection 546 may be established between remote device 508 and number of server systems 512.

Secure wireless connection 544 and secure wireless connection 546 may each be comprised of one or more wireless communications links. Further, secure wireless connection 544 and secure wireless connection 546 may be included as part of number of secure wireless connections 522. In this manner, number of secure wireless connections 522 may enable communications between onboard device 506 and remote device 508 directly, indirectly, or both.

Interactive interface 547 enables communications between device operator 518 using onboard device 506 and medical professional 520 using remote device 508. Interactive interface 547 may take the form of conference session 548 in one illustrative example. In this example, conference server system 550 in number of server systems 512 is used to establish conference session 548. Conference session 548 may include video capabilities, audio capabilities, chat capabilities, or a combination thereof, depending on the implementation.

For example, conference session 548 may be a video conference session that enables device operator 518 to communicate directly with medical professional 520. Device operator 518 may communicate at least a portion of information 524 to medical professional 520 through conference session 548. Further, depending on the circumstances, the video conference session may also allow medical professional 520 to remotely observe person 504 experiencing set of symptoms 505.

In some illustrative examples, medical assessment 526 of medical event 502 may be communicated by medical professional 520 to device operator 518 through conference session 548. In other illustrative examples, medical professional 520 may send medical assessment 526 from remote device 508 to onboard device 506 directly over number of secure wireless connections 522 in the form of a report.

In these illustrative examples, each of the different secure wireless connections described above may be established using any of a number of different means. Further, any number of security measures may be implemented in association with any one of these secure wireless connections. As one illustrative example, a security measure may be implemented in association with secure wireless connection 540. This security measure may be considered separate from or part of the process of establishing secure wireless connection 540.

The security measure may include, for example, without limitation, at least one of a firewall, an intrusion prevention system, anti-virus software, authentication requirements, certificate validation requirements, or some other type security system. Depending on the implementation, satisfying the security measure may include, but is not limited to, certificate validation; key authentication; authentication of the identify of at least one of device operator 518, onboard device 506, or aircraft 501; confirmation of a tail identifier for aircraft 501; authentication of aircraft 501 based on at least a portion of Out, Off, On, In (OOOI) data for aircraft 501; conformation that aircraft 501 is in a phase of flight 503; or some type action.

In some illustrative examples, secure wireless connection 540 may be unable to be established between onboard device 506 and medical data storage infrastructure 510 until at least one of device operator 518, onboard device 506, or aircraft 501 has been authenticated by authenticating system 552. Authenticating system 552 may be, for example, a back-office server system, an airline computer system, or some other type of system. Airline computer system 204 in FIG. 2 may be an example of one implementation for this type of authenticating system 552.

As one illustrative example, device operator 518 may use a security token to establish secure wireless connection 540 between onboard device 506 and authenticating system 552. The security token may take the form of a hardware security token or a software security token, depending on the implementation.

For example, the security token may include, without limitation, a Universal Serial Bus (USB) token, a key fob, an authentication token, a cryptographic token, a virtual token, a cryptographic key, a digital signature, biometric data, some other type of hardware device, some other type of software component, or some combination thereof. In one illustrative example, the security taken may take the form of a Universal Serial Bus (USB) token that generates a revolving random key that may be used to authenticate onboard device 506. In this illustrative example, secure wireless connection 540 may only be established after onboard device 506 has been authenticated by authenticating system 552.

In this manner, aircraft medical management system 500 may be implemented in any number of different ways to provide medical assistance to persons onboard an aircraft, such as aircraft 501. Depending on the implementation, aircraft medical management system 500 may include multiple onboard devices for use with multiple aircraft, multiple remote devices for use by multiple medical professionals, or some combination thereof.

Aircraft medical management system 500 may reduce the time needed to medically attend to persons experiencing symptoms onboard an aircraft. Further, aircraft medical management system 500 may improve the decision-making that is performed onboard an aircraft in response to medical events. For example, the decision-making with respect to when aircraft 501 is to be diverted or when aircraft 501 is to turn back around and return to a starting point may be improved. With this improved decision-making, the medical care provided to persons onboard an aircraft may be improved. Further, with this improved decision-making, cost savings for the airline may be achieved.

In some cases, person 504 may not have previously opted to have their medical data transferred to and stored in medical data storage infrastructure 510. Further, person 504 may not have previously authorized that certain actions be allowed to be taken by device operator 518 or some other crew member onboard aircraft 501. In these types of situations, default procedures may be put in place for providing medical assistance to person 504.

For example, when medical event 502 that occurs onboard aircraft 501 is an emergency medical event involving person 504 or some other type of life-threatening or severe medical event involving person 504, device operator 518 may implement default procedures for communicating with medical professional 520 using onboard device 506, diverting aircraft 501 to an alternate destination in proximity to a nearest on-ground medical center, or both. In this manner, onboard device 506 may be used to provide medical care to person 504 even if person 504 has not opted into the usage of medical data storage infrastructure 510.

The illustration of aircraft medical management system 500 in FIG. 5 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, conference session 548 may not be needed in some cases. In some illustrative examples, onboard device 506 may have connection manger 554 that is used to manage any secure wireless connections established between onboard device 506 and devices or systems. Connection manager 554 may be implemented using hardware, software, firmware, or some combination thereof, depending on the implementation.

In other illustrative examples, conference session 548 may be established through cloud computing. For example, a conference cloud may serve as a relay point for conference session 548 between onboard device 506 and remote device 508.

In some illustrative examples, data 535 stored in medical data storage infrastructure 510 may be updated over time. For example, medical data 536 and additional personal data 538 for person 504 may be updated as this data changes for person 504 over time.

In some illustrative examples, data 535 stored in medical data storage infrastructure 510 may include data about medical events that occurred on the various aircraft belonging to an airline or multiple airlines. For example, when person 504 is involved in medical event 502 that occurs onboard aircraft 501, information about medical event 502, the handling of medical event 502, and the resolution of medical event 502 may be recorded and stored in medical data storage infrastructure 510. This type of data may be available for future use in improving the manner in which medical care is provided to persons.

Figure 6:
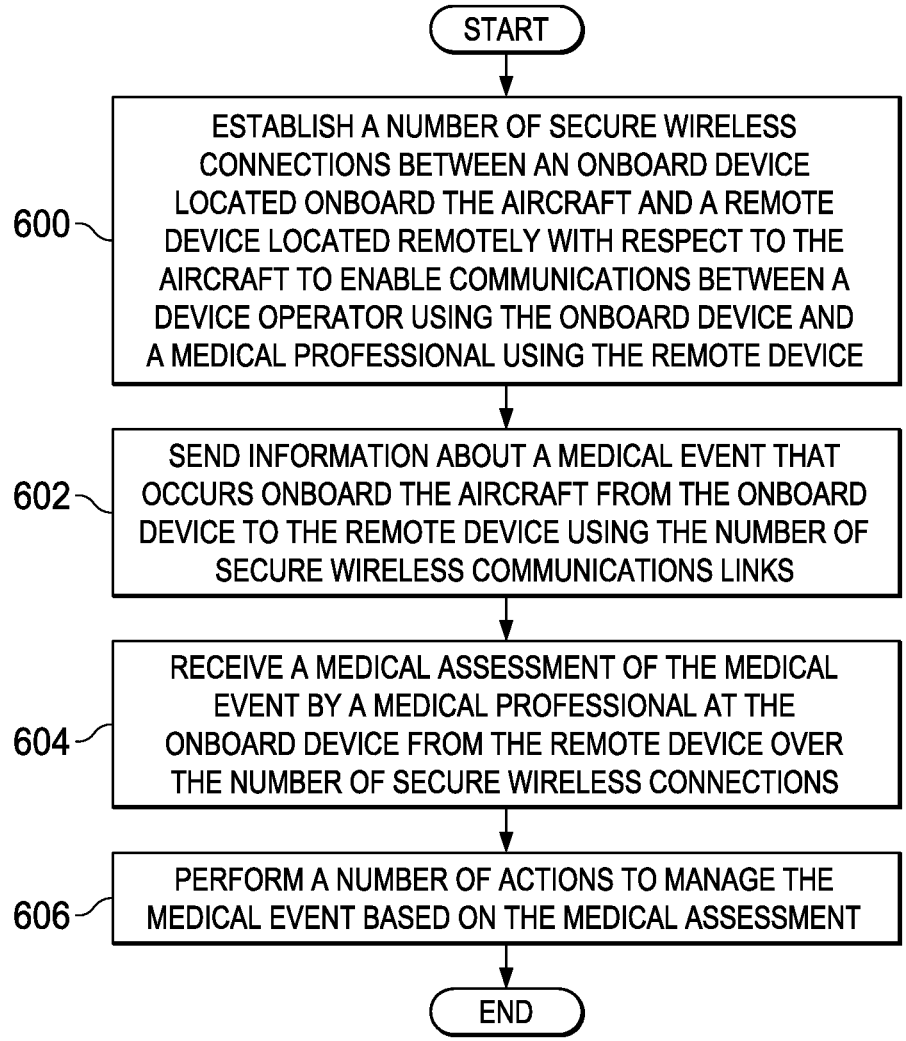
FIG. 6 is an illustration of a process for providing medical assistance onboard an aircraft in the form of a flowchart in accordance with an illustrative embodiment.

With reference now to FIG. 6, an illustration of a process for providing medical assistance onboard an aircraft is depicted in the form of a flowchart in accordance with an illustrative embodiment. The process illustrated in FIG. 6 may be implemented using aircraft medical management system 500 described in FIG. 5.

The process begins by establishing a number of secure wireless connections between an onboard device located on the aircraft and a remote device located remotely with respect to the aircraft, to enable communications between a device operator using the onboard device and a medical professional using the remote device (operation 600). Next, information about a medical event that occurs onboard the aircraft is sent from the onboard device to the remote device using the number of secure wireless communications links (operation 602).

A medical assessment of the medical event by a medical professional is received at the onboard device from the remote device over the number of secure wireless connections (operation 604). A number of actions may then be performed to manage the medical event based on the medical assessment (operation 606), with the process terminating thereafter.

Figure 7:
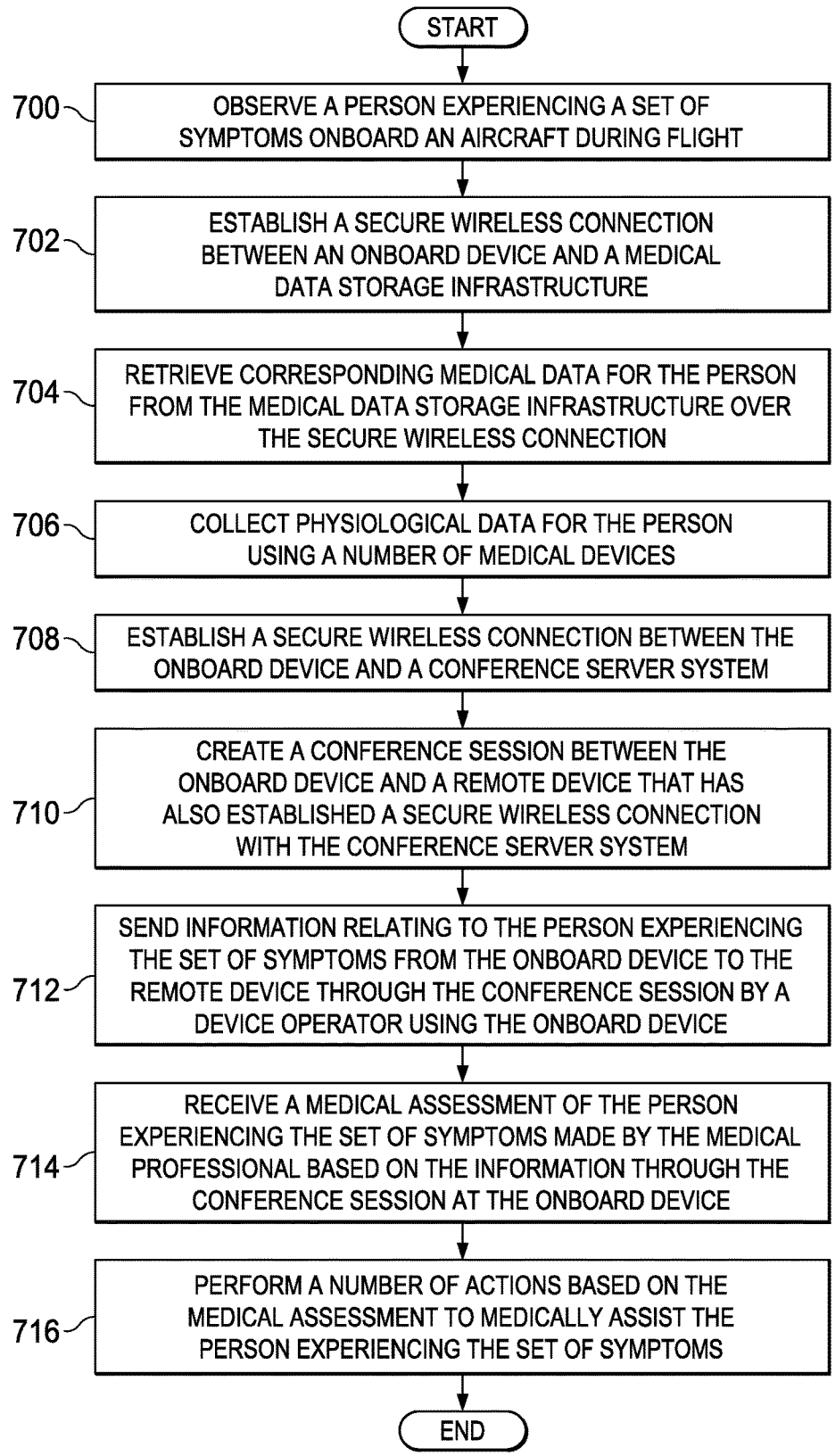
FIG. 7 is an illustration of a process for providing medical assistance to a person onboard an aircraft in the form of a flowchart in accordance with an illustrative embodiment.

With reference now to FIG. 7, an illustration of a process for providing medical assistance to a person onboard an aircraft is depicted in the form of a flowchart in accordance with an illustrative embodiment. The process illustrated in FIG. 7 may be implemented using aircraft medical management system 500 described in FIG. 5.

The process begins by observing a person experiencing a set of symptoms onboard an aircraft during flight (operation 700). In response to this observation, a secure wireless connection is established between an onboard device and a medical data storage infrastructure (operation 702). Corresponding medical data for the person is retrieved from the medical data storage infrastructure over the secure wireless connection (operation 704).

Next, physiological data is collected for the person using a number of medical devices (operation 706). In operation 706, the physiological data may include, for example, without limitation, a temperature of the person, blood pressure information, hearing test data, eye test data, electrocardiogram data, other types of physiological data, or some combination thereof.

Thereafter, a secure wireless connection is established between the onboard device and a conference server system (operation 708). A conference session is created between the onboard device and a remote device that has also established a secure wireless connection with the conference server system (operation 710).

Information relating to the person experiencing the set of symptoms is sent from the onboard device to the remote device through the conference session by a device operator using the onboard device (operation 712). In one illustrative example, operation 712, the information may be communicated by the device operator to the medical professional through the conference session in verbal form, visual form, or both. In operation 712, this information may include at least a portion of the corresponding medical data retrieved from the medical data storage infrastructure, at least a portion of the physiological data collected using the number of onboard devices, other information about the person, or some combination thereof.

In response to receiving this information, a medical assessment of the person experiencing the set of symptoms made by the medical profession based on the information is received through the conference session at the onboard device (operation 714). In operation 714, the medical assessment may be communicated to the device operator by the medical operator through the conference session in verbal form, visual form, or both. A number of actions may then be performed based on the medical assessment to medically assist the person experiencing the set of symptoms (operation 716), with the process terminating thereafter.

Figure 8:
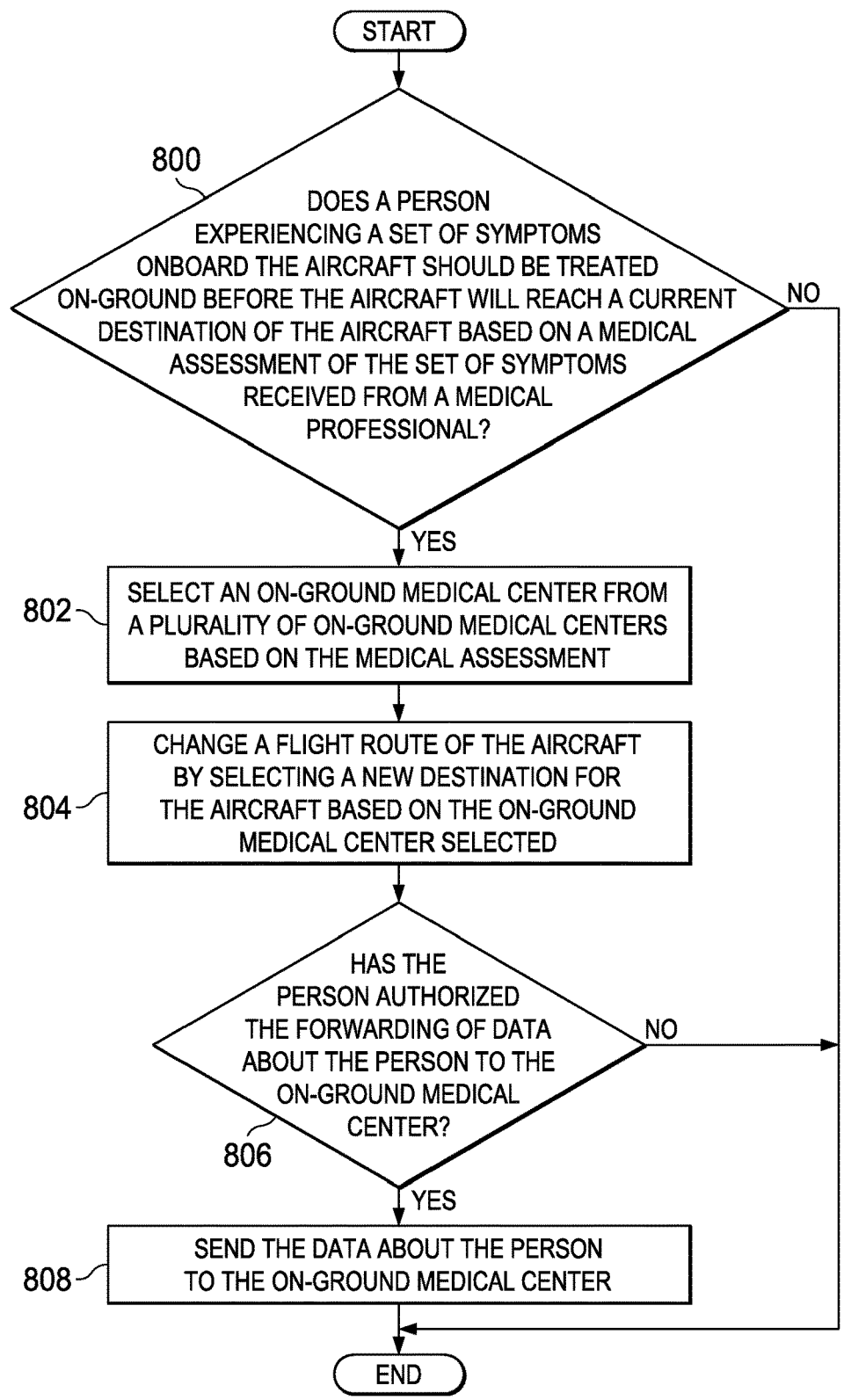
FIG. 8 is an illustration of a process for determining whether a flight route for an aircraft needs to be changed for a person experiencing a set of symptoms onboard an aircraft in the form of a flowchart in accordance with an illustrative embodiment.

With reference now to FIG. 8, an illustration of a process for determining whether a flight route for an aircraft needs to be changed for a person experiencing a set of symptoms onboard an aircraft is depicted in the form of a flowchart in accordance with an illustrative embodiment. The process illustrated in FIG. 8 may be an example one manner in which operation 716 in FIG. 7 may be performed.

The process begins by determining whether a person experiencing a set of symptoms onboard the aircraft should be treated on-ground before the aircraft will reach a current destination of the aircraft based on a medical assessment of the set of symptoms received from a medical professional (operation 800). The medical assessment described in FIG. 8 may be, for example, the medical assessment received in operation 714 in FIG. 7.

If the person does not need to be treated on-ground before the aircraft will reach the current destination, the flight route for the aircraft does not need to be changed and the determination process terminates. Otherwise, in response to a determination that the person should be treated on-ground before the aircraft will reach the current destination, an on-ground medical center is selected from a plurality of on-ground medical centers based on the medical assessment (operation 802). The plurality of on-ground medical centers may include a list of hospitals, clinics, emergency clinics, other types of medical centers, or some combination thereof.

The selection of an on-ground medical center in operation 802 may be performed in any number of ways. In one illustrative example, the on-ground medical center is selected based on at least one of a current position of the aircraft and proximity of the on-ground medical center to the current position of the aircraft, a heading of the aircraft, an altitude of the aircraft, a fuel status of the aircraft, an approved route structure for the aircraft, a passenger manifest, an airport or other suitable landing area in proximity to the on-ground medical center, or a number of aircraft capability factors. In some cases, health insurance information for the person may be used to select an on-ground medical center. For example, when the medical condition of the person is not life-threatening, a choice may be made to select an in-network on-ground medical center that may be located farther away than an out-of-network on-ground medical center.

Next, a flight route of the aircraft is changed by selecting a new destination for the aircraft based on the on-ground medical center selected (operation 804). The new destination may be the on-ground medical center, an airport near the on-ground medical center, an airfield near the on-ground medical center, or some other area near the on-ground medical center.

Thereafter, a determination may be made as to whether the person has authorized the forwarding of data about the person to the on-ground medical center (operation 806). For example, the person may have authorized that their medical data be forwarded to any on-ground medical center as needed, only specifically identified on-ground medical centers, or the closest on-ground medical center upon arrival at any authorized destination. In some illustrative examples, a record of this authorization may be stored in the medical data storage infrastructure from which the medical data for the person was retrieved.

If the person has not authorized forwarding of the data, the process terminates. In this manner, the flight route of the aircraft is changed such that the person can be taken to the on-ground medical center for treatment but their medical data may not be sent to the on-ground medical center prior to their arrival.

With reference again to operation 806, if the person has authorized forwarding of the data, the data about the person is sent to the on-ground medical center in response (operation 808), with the process terminating thereafter. The data may include at least one of medical data, physiological data, mental health data or other personal data about the person.

Figure 9:
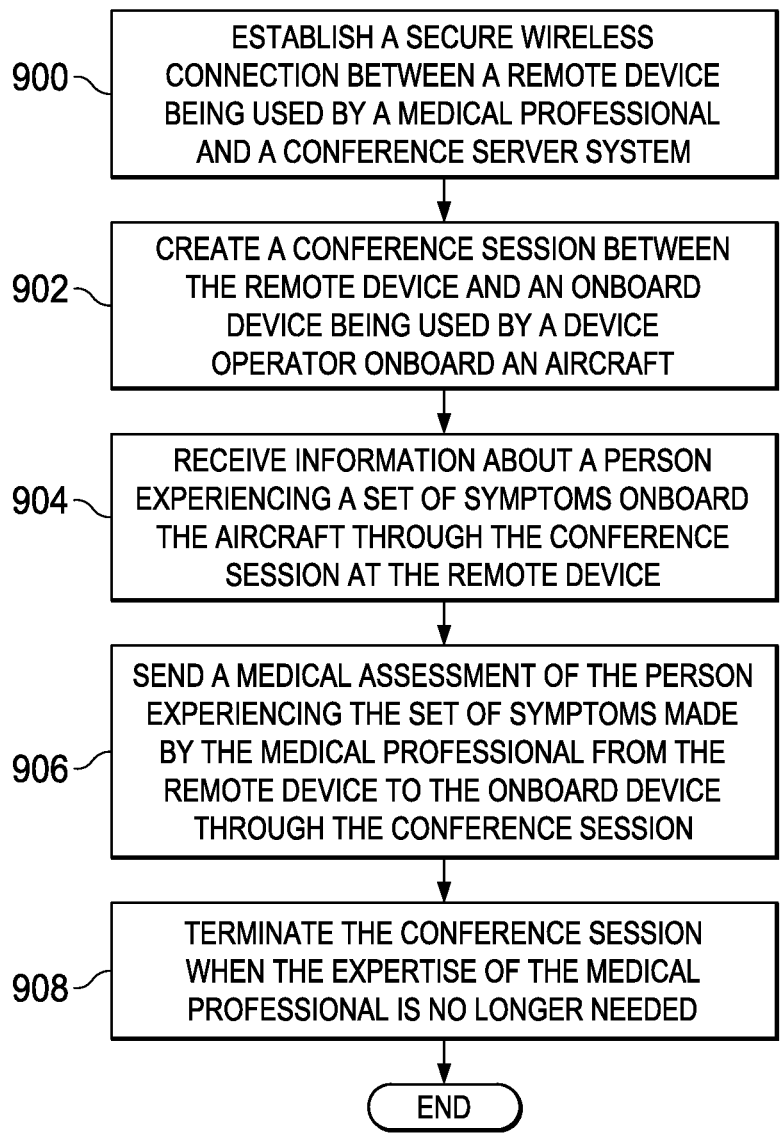
FIG. 9 is an illustration of a process for remotely assessing a person experiencing a set of symptoms onboard an aircraft in the form of a flowchart in accordance with an illustrative embodiment.

With reference now to FIG. 9, an illustration of a process for remotely assessing a person experiencing a set of symptoms onboard an aircraft is depicted in the form of a flowchart in accordance with an illustrative embodiment. The process illustrated in FIG. 9 may be implemented using a remote device, such as remote device 510 in FIG. 5.

The process begins by establishing a secure wireless connection between a remote device being used by a medical professional and a conference server system (operation 900). Next, a conference session is created between the remote device and an onboard device being used by a device operator onboard an aircraft (operation 902). In operation 902, the onboard device is also securely and wirelessly connected to the conference server system. The conference server system serves as a relay point between the onboard device and the remote device.

Next, information about a person experiencing a set of symptoms onboard the aircraft is received through the conference session at the remote device (operation 904). Then, a medical assessment of the person experiencing the set of symptoms made by the medical professional is sent from the remote device to the onboard device (operation 906). The conference session is then terminated when the expertise of the medical professional is no longer needed (operation 908), with the process terminating thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in some cases, operation 708 and operation 710 in FIG. 7 may be performed prior to operation 706 in FIG. 7 such that the conference session is created before physiological data is collected for the person. In some cases, establishing the conference session first may enable the medical professional to instruct the device operator with respect to what types of physiological data need to be collected and how to collect the physiological data.

Figure 10:
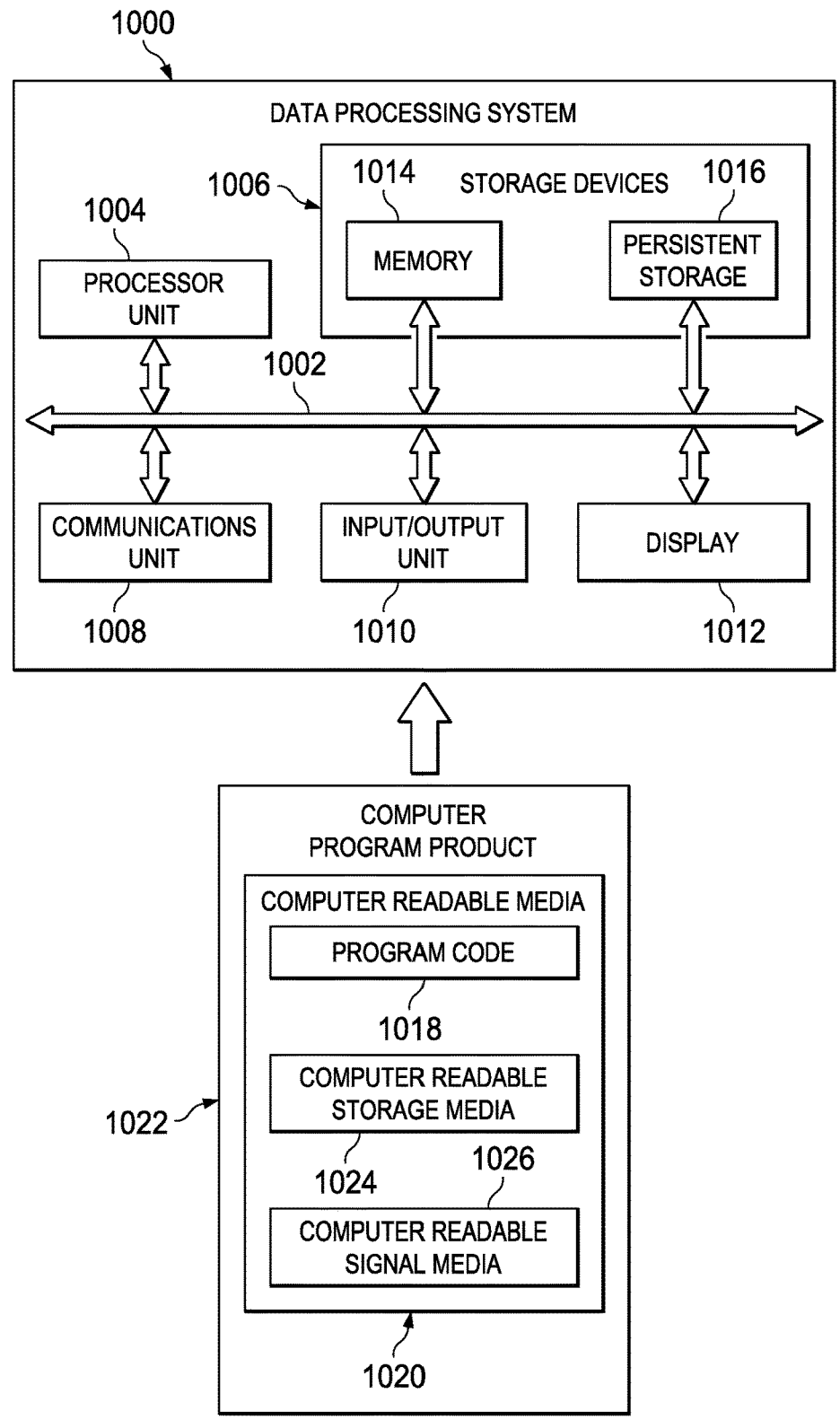
FIG. 10 is an illustration of a data processing system in the form of a block diagram in accordance with an illustrative embodiment.

Turning now to FIG. 10, an illustration of a data processing system in the form of a block diagram is depicted in accordance with an illustrative embodiment. Data processing system 1000 may be used to implement onboard device 506, remote device 508, or both in FIG. 5. As depicted, data processing system 1000 includes communications framework 1002, which provides communications between processor unit 1004, storage devices 1006, communications unit 1008, input/output unit 1010, and display 1012. In some cases, communications framework 1002 may be implemented as a bus system.

Processor unit 1004 is configured to execute instructions for software to perform a number of operations. Processor unit 1004 may comprise a number of processors, a multi-processor core, and/or some other type of processor, depending on the implementation. In some cases, processor unit 1004 may take the form of a hardware unit, such as a circuit system, an application specific integrated circuit (ASIC), a programmable logic device, or some other suitable type of hardware unit.

Instructions for the operating system, applications, and/or programs run by processor unit 1004 may be located in storage devices 1006. Storage devices 1006 may be in communication with processor unit 1004 through communications framework 1002. As used herein, a storage device, also referred to as a computer readable storage device, is any piece of hardware capable of storing information on a temporary and/or permanent basis. This information may include, but is not limited to, data, program code, and/or other information.

Memory 1014 and persistent storage 1016 are examples of storage devices 1006. Memory 1014 may take the form of, for example, a random access memory or some type of volatile or non-volatile storage device. Persistent storage 1016 may comprise any number of components or devices. For example, persistent storage 1016 may comprise a hard drive, a flash memory, a rewritable optical disk, a rewritable magnetic tape, or some combination of the above. The media used by persistent storage 1016 may or may not be removable.

Communications unit 1008 allows data processing system 1000 to communicate with other data processing systems and/or devices. Communications unit 1008 may provide communications using physical and/or wireless communications links.

Input/output unit 1010 allows input to be received from and output to be sent to other devices connected to data processing system 1000. For example, input/output unit 1010 may allow user input to be received through a keyboard, a mouse, and/or some other type of input device. As another example, input/output unit 1010 may allow output to be sent to a printer connected to data processing system 1000.

Display 1012 is configured to display information to a user. Display 1012 may comprise, for example, without limitation, a monitor, a touch screen, a laser display, a holographic display, a virtual display device, and/or some other type of display device.

In this illustrative example, the processes of the different illustrative embodiments may be performed by processor unit 1004 using computer-implemented instructions. These instructions may be referred to as program code, computer usable program code, or computer readable program code and may be read and executed by one or more processors in processor unit 1004.

In these examples, program code 1018 is located in a functional form on computer readable media 1020, which is selectively removable, and may be loaded onto or transferred to data processing system 1000 for execution by processor unit 1004. Program code 1018 and computer readable media 1020 together form computer program product 1022. In this illustrative example, computer readable media 1020 may be computer readable storage media 1024 or computer readable signal media 1026.

Computer readable storage media 1024 is a physical or tangible storage device used to store program code 1018 rather than a medium that propagates or transmits program code 1018. Computer readable storage media 1024 may be, for example, without limitation, an optical or magnetic disk or a persistent storage device that is connected to data processing system 1000.

Alternatively, program code 1018 may be transferred to data processing system 1000 using computer readable signal media 1026. Computer readable signal media 1026 may be, for example, a propagated data signal containing program code 1018. This data signal may be an electromagnetic signal, an optical signal, and/or some other type of signal that can be transmitted over physical and/or wireless communications links.

The illustration of data processing system 1000 in FIG. 10 is not meant to provide architectural limitations to the manner in which the illustrative embodiments may be implemented. The different illustrative embodiments may be implemented in a data processing system that includes components in addition to or in place of those illustrated for data processing system 10. Further, components shown in FIG. 10 may be varied from the illustrative examples shown.

Thus, the illustrative embodiments provide an aircraft medical management system for providing in-flight medical assistance. In particular, the illustrative embodiments provide a method and system for providing live, substantially real-time medical assistance to one or more persons experiencing symptoms onboard an aircraft during flight.

In one illustrative example, this live medical assistance is provided onboard an aircraft via a secure video conference link between an onboard device located on the aircraft and a remote device located off-board. All communications between the onboard device and the remote device may be secure. In this manner, confidentiality of medical data may be maintained during communications between the device operator using the onboard device and the medical professional using the remote device.

In some illustrative examples, persons onboard an aircraft may have had the option to opt-in to have their medical history uploaded to secure medical data cloud storage. Access to this medical data storage cloud may require satisfying any number of security measures. For example, an out of band two-factor authentication may be required before medical data can be retrieved from the medical data storage cloud. Further, a similar type of two-factor authentication may be required to send this medical data from an onboard device to a remote device being used by a medical professional.

In one illustrative example, a medical data storage infrastructure that stores medical data about individuals is provided. The medical data storage infrastructure may be capable of securely and wirelessly connecting to an onboard device located on an aircraft or other airborne vehicle.

For example, a secure wireless connection may be established between the onboard device and the medical data storage infrastructure to enable retrieval, by the onboard device, of medical data about an individual from the medical data storage infrastructure. In some cases, a secure wireless connection may be established between the medical data storage infrastructure and a remote device located off-board with respect to an aircraft to enable retrieval, by the remote device, of medical data about an individual located onboard the aircraft from the medical data storage infrastructure for use in providing medical assistance to the individual.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for providing medical assistance onboard an aircraft, the method comprising:

receiving, prior to a flight of the aircraft, in an airline computer system, an authorization to transfer medical data into a medical storage data infrastructure comprising policies;

a policy in the policies comprising at least one of: a set of rules, a set of guidelines, a set of restrictions, a set of authorizations, or a set of criteria, determining which medical data may: be accessed by each of an onboard device located on the aircraft and a remote device located remotely from the aircraft, or transferred: from the medical storage data infrastructure to the onboard device or the remote device, or between the onboard device and the remote device;

establishing a first wireless connection between the onboard device located on the aircraft and the airline computer system located remotely with respect to the aircraft and the remote device, the airline computer system comprising an intrusion prevention system for preventing unauthorized devices from connecting wirelessly to the airline computer system, and the onboard device comprising an authorization acceptable to the airline computer system for enabling communications with the onboard device;

preventing, until completion of a security measure comprising the airline computer system authenticating at least one of an identity of the onboard device or of the aircraft comprising the onboard device, the onboard device from accessing a medical data storage infrastructure, the medical storage data infrastructure being located remote from the aircraft and the airline computer system, and comprising medical data, about a person on the aircraft, authorized, prior to the flight, for at least one of:

transfer into the medical data storage infrastructure;

transfer from the medical data storage infrastructure to the remote device; and transfer from the medical data storage infrastructure to a onboard device after the airline computer system accepts the authorization from the onboard device;

preventing, until completion of a security measure comprising the medical data storage infrastructure authenticating at least one of the identity of the onboard device or of the aircraft comprising the onboard device, the onboard device from accessing the medical data storage infrastructure:

the onboard device connecting to the medical data storage infrastructure via a second wireless connection comprising an intrusion prevention system for preventing unauthorized devices from connecting wirelessly to the medical data storage infrastructure, and the onboard device comprising a certificate acceptable to the medical data storage infrastructure for enabling communications with the onboard device;

subsequently, establishing communications, using a third wireless connection, between the onboard device and the remote device in communication with a medical professional via:

the onboard device comprising an intrusion prevention system for preventing unauthorized devices from connecting wirelessly to the onboard device via the onboard device validating a certificate from the remote device for enabling communications with the onboard device; and the remote device comprising an intrusion prevention system for preventing unauthorized devices from connecting wirelessly to the remote device via the remote device validating a certificate from the onboard device for enabling communications with the remote device;

sending, information, comprising information about the aircraft and an output, from a medical device onboard the aircraft about a medical event onboard the aircraft from the onboard device to the remote device, the medical device communicating with the onboard device and selected from a group comprising: a digital thermometer, an electronic stethoscope, an electrocardiogram machine, a tympanometric instrument, a sphygmomanometer, an otoscope, an ophthalmoscope, a pulse oximeter, a vital signs monitor, and a diagnostic station;

responsive to receiving a Health Insurance Portability and Accountability Act compliant authorization to transfer medical data related to the medical event from the medical data storage infrastructure to the remote device, transferring medical data related to the medical event from the medical data storage infrastructure to the remote device;

receiving, at the onboard device, a medical assessment of the medical event and a medical professional directed action, from the remote device;

executing the medical professional directed action onboard the aircraft;

directing, using the medical assessment, a route for the aircraft; and flying the aircraft on the route.

2. The method of claim 1 further comprising:
directing, using health insurance information for a person associated with the medical event, the route for the aircraft;
the remote device communicating, using a set of policies, with a previously loaded medical data storage infrastructure; and
using the medical data storage infrastructure for deriving the medical assessment.

3. The method of claim 1 further comprising:
the medical device further comprising: a laryngoscope, an x-ray machine, d aan ultrasound device; and collecting, using the medical device, physiological data and a set of symptoms related to the medical event onboard the aircraft.

4. The method of claim 3 further comprising:
sending the physiological data from the onboard device to the remote device and using the physiological data for formulating the medical assessment for the set of symptoms.

5. The method of claim 1 further comprising:
establishing a secure wireless connection between the medical data storage infrastructure storing medical data for a number of persons onboard the aircraft and the remote device; and
authenticating between the onboard device and the airline computer system, at least one of: an identity of a user of the onboard device, a tail identifier for the aircraft; at least a portion of Out, Off, On, In, data for the aircraft confirming a phase of flight for the aircraft.

6. The method of claim 5 further comprising:
retrieving, from the medical data storage infrastructure over the secure wireless connection by the at least one of the onboard device or the remote device, corresponding medical data pertaining to the medical event onboard the aircraft.

7. The method of claim 1, -further comprising performing a number of actions based on the medical assessment to at least one of: isolate, treat, or advise onboard the aircraft.

8. The method of claim 1 further comprising:
determining whether the person should be treated on-ground before the aircraft will reach a current destination;
selecting an on-ground medical center from a plurality of on-ground medical centers based on the medical assessment in response to a determination that the person should be treated on-ground before the aircraft will reach the current destination; and
changing the route of the aircraft by selecting a new destination for the aircraft based on the on-ground medical center selected.

9. The method of claim 8, -further comprising:
determining whether the person has authorized forwarding data about the person to the on-ground medical center; and
sending the data about the person to the on-ground medical center in response to a determination that the person has authorized forwarding the data about the person to the on-ground medical center, wherein the data includes at least one of medical data, mental health data, physiological data, or personal data about the person.

10. The method of claim 8, wherein selecting the on-ground medical center comprises:
selecting the on-ground medical center based on at least one of: a fuel status of the aircraft, an approved route structure for the aircraft, a passenger manifest, and a nearest airport to the on-ground medical center.

11. The method of claim 1, further comprising:
establishing a first secure wireless connection between the onboard device, comprising a mobile computer system, and a conference server system; and
establishing a second secure wireless connection between the conference server system and the remote device comprising a remote computer system.

12. The method of claim 10 further comprising receiving the medical assessment pertaining to the person through a conference session established between the remote device and the onboard device through a conference server system.

13. A method for reducing a time, on an aircraft during flight, between an observation of medical symptoms of a medical event related to a person experiencing a set of symptoms on the aircraft and an initiation of a medical professional directed action using a medical assessment of the symptoms, the method comprising:
receiving, prior to the flight of the aircraft, in an airline computer system, an authorization to transfer medical data into a medical storage data infrastructure comprising policies;
a policy in the policies comprising at least one of: a set of rules, a set of guidelines, a set of restrictions, a set of authorizations, or a set of criteria, determining which medical data may: be accessed by each of an onboard device located on the aircraft and a remote device located remotely from the aircraft, or transferred: from the medical storage data infrastructure to the onboard device or the remote device, or between the onboard device and the remote device;
establishing a first wireless connection between the onboard device located on the aircraft and the airline computer system located remotely with respect to the aircraft and the remote device, the airline computer system comprising an intrusion prevention system for preventing unauthorized devices from connecting wirelessly to the airline computer system, and the onboard device comprising an authorization acceptable to the airline computer system for enabling communications with the onboard device;
preventing, until completion of a security measure comprising the airline computer system authenticating at least one of an identity of the onboard device or of the aircraft comprising the onboard device, the onboard device from accessing a medical data storage infrastructure, the medical storage data infrastructure being located remote from the aircraft and the airline computer system, and comprising medical data, about a person on the aircraft, authorized, prior to the flight, for at least one of:
transfer into the medical data storage infrastructure;
transfer from the medical data storage infrastructure to the remote device; and
transfer from the medical data storage infrastructure to the onboard device after the airline computer system accepts the authorization from the onboard device;
preventing, until completion of a security measure comprising the medical data storage infrastructure authenticating at least one of the identity of the onboard device or of the aircraft comprising the onboard device, the onboard device from accessing the medical data storage infrastructure:
the onboard device connecting to the medical data storage infrastructure via a second wireless connection comprising an intrusion prevention system for preventing unauthorized devices from connecting wirelessly to the medical data storage infrastructure, and the onboard device comprising a certificate acceptable to the medical data storage infrastructure for enabling communications with the onboard device;
subsequently, establishing communications, using a third wireless connection, between the onboard device and the remote device in communication with a medical professional via:
the onboard device comprising an intrusion prevention system for preventing unauthorized devices from connecting wirelessly to the onboard device via the onboard device validating a certificate from the remote device for enabling communications with the onboard device; and
the remote device comprising an intrusion prevention system for preventing unauthorized devices from connecting wirelessly to the remote device via the remote device validating a certificate from the onboard device for enabling communications with the remote device;
generating, using the onboard device communicating with a medical device selected from a group comprising: a digital thermometer, an electronic stethoscope, an electrocardiogram machine, a tympanometric instrument, a sphygmomanometer, an otoscope, an ophthalmoscope, a pulse oximeter, a vital signs monitor, and a diagnostic station, physiological data for the medical event related to the person experiencing the set of symptoms during the flight;
responsive to receiving a Health Insurance Portability and Accountability Act compliant authorization to transfer physiological data related to the medical event, sending the physiological data from the onboard device to the remote device during the flight;
receiving, the medical assessment and the medical professional directed action, formulated using the physiological data from the remote device;
performing the medical professional directed action onboard the aircraft during the flight based on the medical assessment;
directing, using: the medical assessment, health insurance information for a person associated with the medical event, and the medical professional directed action, a route for the aircraft; and
flying the aircraft on the route.

14. An aircraft medical management system that comprises an onboard device, located on an aircraft, that comprises:
an airline computer system configured to receive, prior to a flight of the aircraft, an authorization to transfer medical data into a medical storage data infrastructure that comprises policies;
a policy, in the policies, that comprises at least one of: a set of rules, a set of guidelines, a set of restrictions, a set of authorizations, or a set of criteria, that determine which medical data may: be accessed by each of the onboard device located on the aircraft and a remote device located remotely from the aircraft, or transferred: from the medical storage data infrastructure to the onboard device or the remote device, or between the onboard device and the remote device;
a first wireless connection between the onboard device and the airline computer system located remotely with respect to the aircraft and the remote device, the airline computer system comprising an intrusion prevention system configured to prevent unauthorized devices from a connection with the airline computer system, such that the onboard device comprises an authorization, acceptable to the airline computer system, that enables communications with the onboard device;
a first security measure that comprises an authentication from the airline computer system of at least one of: an identity of the onboard device or of the aircraft, such that an access, by the onboard device, to a medical data storage infrastructure requires the authentication from the airline computer system, the medical storage data infrastructure being: located remote from the aircraft and the airline computer system, and comprising medical data, about a person on the aircraft, authorized, prior to the flight, for at least one of:
- transfer into the medical data storage infrastructure;
- transfer from the medical data storage infrastructure to the remote device; and
- transfer from the medical data storage infrastructure to the onboard device after the airline computer system accepts the authorization from the onboard device;

a second security measure that comprises an authentication from the medical storage data infrastructure of at least one of: the identity of the onboard device or of the aircraft that comprises the onboard device, such that the access, by the onboard device, to the medical data storage infrastructure requires the authentication from the medical data storage infrastructure;

a connection between the onboard device and the medical data storage infrastructure via a second wireless connection that comprises an intrusion prevention system configured to prevent a connection by unauthorized devices to the medical data storage infrastructure, such that the onboard device comprises a certificate acceptable to the medical data storage infrastructure to allow communications with the onboard device;

a third wireless connection, between the onboard device and the remote device in communication with a medical professional, such that the onboard device comprises an intrusion prevention system configured to prevent unauthorized devices from a connection with the onboard device via:
- a validation requirement by the onboard device of a certificate from the remote device; and
- an intrusion prevention system in the remote device configured to prevent unauthorized devices from a connection with the remote device via a validation requirement by the remote device of a certificate from the onboard device;

an interactive interface on the onboard device configured to receive:
- a medical assessment of a set of symptoms related to a medical event onboard the aircraft; and
- a medical professional directed action based upon the access to the medical data storage infrastructure during the flight, such that the medical professional directed action comprises a determination of whether a person experiencing a set of symptoms onboard the aircraft should be treated on-ground before the aircraft will reach a current destination of the aircraft; and authenticate, with the airline computer system, at least one of: an identity of a user of the onboard device, a tail identifier for the aircraft; at least a portion of Out, Off, On, In, data for the aircraft; a phase of flight for the aircraft;

a medical kit and a medical device, each configured to perform a portion of the medical professional directed action onboard the aircraft; and an indicator for a route, based upon the medical assessment and the medical professional directed action, for the aircraft to fly responsive to the medical event onboard the aircraft.

15. The aircraft medical management system of claim 14, wherein the medical assessment comprises a number of actions to assist the person experiencing a set of symptoms onboard the aircraft during the flight.

16. The aircraft medical management system of claim 14, further comprising:
a number of medical devices in communication with the onboard device and configured to generate physiological data, such that the number of medical devices comprises at least one of:
a digital thermometer, an electronic stethoscope, an electrocardiogram machine, a tympanometric instrument, a sphygmomanometer, an otoscope, an ophthalmoscope, a pulse oximeter, a vital signs monitor, a laryngoscope, a penlight, or a diagnostic station.

17. The aircraft medical management system of claim 14, further comprising:
the medical data storage infrastructure configured to store medical data about the person, the onboard device configured to:
establish a secure wireless connection between the onboard device and the medical data storage infrastructure; and
enable retrieval from the medical data storage infrastructure, of the medical data about the person.

18. The aircraft medical management system of claim 14, wherein the medical assessment comprises at least one of: a medical diagnosis, a number of isolation instructions, a number of treatment instructions, or a number of advising instructions.

19. The aircraft medical management system of claim 14, wherein the onboard device is a mobile computer system selected from one of a smartphone, a tablet, a laptop, and a tablet-laptop hybrid.

20. The aircraft medical management system of claim 14, further comprising:
a conference server system;
a first secure wireless connection between the onboard device and the conference server system; and
a second secure wireless connection between the conference server system and the remote device.

* * * * *